US011973643B2

(12) United States Patent
Baturin

(10) Patent No.: US 11,973,643 B2
(45) Date of Patent: *Apr. 30, 2024

(54) DISTRIBUTED DATA STORAGE TECHNIQUES FOR EDGE DEVICES

(71) Applicant: Oracle International Corporation, Redwood Shores, CA (US)

(72) Inventor: Maxim Baturin, Sammamish, WA (US)

(73) Assignee: Oracle International Corporation, Redwood Shores, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/330,227

(22) Filed: Jun. 6, 2023

(65) Prior Publication Data

US 2023/0327948 A1    Oct. 12, 2023

Related U.S. Application Data

(63) Continuation of application No. 17/565,337, filed on Dec. 29, 2021, now Pat. No. 11,777,796.
(Continued)

(51) Int. Cl.
*H04L 41/0806* (2022.01)
*G06F 3/06* (2006.01)
(Continued)

(52) U.S. Cl.
CPC ........ *H04L 41/0806* (2013.01); *G06F 3/0604* (2013.01); *G06F 3/0622* (2013.01);
(Continued)

(58) Field of Classification Search
None
See application file for complete search history.

(56) References Cited

U.S. PATENT DOCUMENTS 8,613,070 B1    12/2013  Borzycki et al.
10,404,613 B1    9/2019  Brooker et al.
(Continued)

OTHER PUBLICATIONS

Li, Danlin. Edge computing, a compensation method for cloud computing on smart grid. Diss. UNSW Sydney, 2020. (Year: 2020).*
(Continued)

*Primary Examiner* — Nicholas J Simonetti
(74) *Attorney, Agent, or Firm* — Kilpatrick Townsend & Stockton LLP

(57) ABSTRACT

Techniques discussed herein relate to implementing a distributed computing cluster (the "cluster") including a plurality of edge devices (e.g., devices individually configured to selectively execute within an isolated computing environment). One edge device may be configured to operate as a head node of the cluster at a given time. A request for virtual resources of the cluster may be received from a user device and directed to the first edge device of the cluster. The first edge device may determine it is not operating as a head node of the cluster. The first edge device may determine that a second edge device of the cluster is operating as the head node. In response, the first edge device may forward the request to the second edge device, wherein forwarding the request to the second edge device causes the second request to be processed by the cluster.

20 Claims, 12 Drawing Sheets

Related U.S. Application Data

(60) Provisional application No. 63/173,244, filed on Apr. 9, 2021.

(51) Int. Cl.

| | | |
|---|---|---|
| *G06F 8/61* | (2018.01) | |
| *G06F 8/658* | (2018.01) | |
| *G06F 9/4401* | (2018.01) | |
| *G06F 9/455* | (2018.01) | |
| *G06F 9/50* | (2006.01) | |
| *G06F 11/14* | (2006.01) | |
| *H04L 9/08* | (2006.01) | |
| *H04L 9/40* | (2022.01) | |
| *H04L 12/46* | (2006.01) | |
| *H04L 67/10* | (2022.01) | |

(52) U.S. Cl.
CPC .......... *G06F 3/0655* (2013.01); *G06F 3/0659* (2013.01); *G06F 3/067* (2013.01); *G06F 3/0679* (2013.01); *G06F 8/61* (2013.01); *G06F 8/658* (2018.02); *G06F 9/4406* (2013.01); *G06F 9/45558* (2013.01); *G06F 9/505* (2013.01); *G06F 9/5055* (2013.01); *G06F 9/5077* (2013.01); *G06F 9/5088* (2013.01); *G06F 11/1451* (2013.01); *G06F 11/1469* (2013.01); *H04L 9/0897* (2013.01); *H04L 12/4641* (2013.01); *H04L 63/0471* (2013.01); *H04L 63/0478* (2013.01); *H04L 63/0485* (2013.01); *H04L 63/06* (2013.01); *H04L 63/0876* (2013.01); *H04L 63/162* (2013.01); *H04L 63/20* (2013.01); *H04L 67/10* (2013.01); *G06F 2009/45562* (2013.01); *G06F 2009/45587* (2013.01); *G06F 2009/45595* (2013.01); *G06F 2201/84* (2013.01)

(56) References Cited

U.S. PATENT DOCUMENTS

| | | |
|---|---|---|
| 11,683,220 B2 | 6/2023 | Maheshwari et al. |
| 11,777,796 B2 | 10/2023 | Baturin |
| 2013/0332927 A1 | 12/2013 | Tang et al. |
| 2015/0378753 A1* | 12/2015 | Phillips ............... G06F 9/505 |
| | | 718/1 |
| 2018/0103088 A1 | 4/2018 | Blainey et al. |
| 2019/0007339 A1 | 1/2019 | Bao et al. |
| 2019/0036687 A1 | 1/2019 | Raza et al. |
| 2023/0011628 A1 | 1/2023 | Hurley et al. |
| 2023/0049501 A1 | 2/2023 | Xu et al. |

OTHER PUBLICATIONS

U.S. Appl. No. 18/296,348, Notice of Allowance, mailed on Dec. 20, 2023, 5 pages.
U.S. Appl. No. 17/531,566, Notice of Allowance mailed on Mar. 21, 2023, 10 pages.
U.S. Appl. No. 17/565,337, Notice of Allowance mailed on May 11, 2023, 11 pages.
U.S. Appl. No. 18/296,348, Non-Final Office Action mailed on Nov. 7, 2023, 10 pages.

* cited by examiner

DISTRIBUTED DATA STORAGE TECHNIQUES FOR EDGE DEVICES

CROSS-REFERENCE TO RELATED APPLICATIONS

This non-provisional application claims priority to U.S. patent application Ser. No. 17/565,337, filed on Dec. 29, 2021, entitled, "Distributed Data Storage Techniques for Edge Devices," and claims benefit of U.S. Provisional Patent Application No. 63/173,244, filed on Apr. 9, 2021, entitled, "Cloud Computing Edge Computing Device (Rover)," the disclosure of which are herein incorporated by reference in their entirety for all purposes.

BACKGROUND

In cloud computing, processing and storage is generally performed by one or more service providers implemented at a centralized location. Data can be received from customers at the centralized location, processed there, and then the processed (or other) data can be transmitted back to customers. However, having a centralized location for cloud infrastructure components may not be ideal in various scenarios. For example, when there are hundreds or thousands of Internet of Things (IoT) devices transmitting data to the central servers, and especially when those IoT devices are not geographically close to the cloud infrastructure computing devices, conventional centralized systems are not ideal. These IoT devices may be considered on the "edge," as in they are not close to the central servers.

Additionally, there may be other instances when the centralized location for cloud components is less than ideal. For example, if the data is collected (e.g., by IoT devices) in a disconnected region or a location with no Internet connectivity (e.g., remote locations). Current centralized cloud computing environments may not meet time sensitivity requirements when streaming data due to the inherent latency of their wide-area network connections. Remotely generated data may need to be processed more quickly (e.g., to detect anomalies) than conventional centralized cloud computing systems allow. Thus, there are challenges with managing a traditional cloud computing environment that relies on centralized components. For example, a centralized workflow manager may be suboptimal for managing workflows at geographically remote devices.

BRIEF SUMMARY

Techniques are provided (e.g., a method, a system, an edge device, a non-transitory computer-readable medium storing code or instructions executable by one or more processors) for updating an edge device (e.g., a computing device configured to deliver computing and storage at remote locations separate from the centralized data center and lacking a public/private network connection). Various embodiments are described herein, including methods, systems, non-transitory computer-readable storage media storing programs, code, or instructions executable by one or more processors, and the like.

One embodiment is directed to a method for processing a request for virtual resources of a distributing computing cluster comprising a plurality of edge devices. The method may comprise implementing, at least in part by a first edge device, a distributed computing cluster including a plurality of edge devices comprising the first edge device. In some embodiments, the distributed computing cluster comprises one edge device configured to operate as a head node of the distributed computing cluster. The plurality of edge devices may be individually configured to selectively execute within an isolated computing environment. In some embodiments, the plurality of edge devices have no access to a public network while executing within the isolated computing environment. The method may further comprise receiving, from a user device and directed to the first edge device, a request for virtual resources of the distributed computing cluster. The method may further comprise determining, by the first edge device, that the first edge device is operating as a computing node different from the head node of the distributed computing cluster. The method may further comprise determining, by the first edge device, that a second edge device of the distributed computing cluster has been elected as the head node of the distributed computing cluster. The method may further comprise forwarding, by the first edge device to the second edge device, the request, wherein forwarding the request to the second edge device causes the request to be processed by the distributed computing cluster.

In some embodiments, each of the plurality of edge devices provide a plurality of object storage devices for data replication. The distributed computing cluster may store key-value pairs that are individually replicated on at least two of the plurality of object storage devices.

In some embodiments, the method further comprises receiving a subsequent request for virtual resources of the distributed computing cluster and determining, by the first edge device, whether the request is a read request or a write request. In some embodiments, the subsequent request is forwarded to the second edge device based at least in part on determining the request is a write request. The first edge device may process the request based at least in part on determining the subsequent request is a read request. In some embodiments, when the subsequent request is a read request, the method may further comprise transmitting, by the first edge device, the read request to a set of remaining computing nodes in the distributed computing cluster. The first edge device may receive a number of responses to the read request from a subset of the distributed computing cluster. The method may further comprise identifying, by the first edge device, that a majority of the distributed computing cluster have responded. The method may further comprise transmitting, by the first edge device, an indication that the read request was successful in response to identifying that the majority of the distributed computing cluster have responded.

In some embodiments, the method may further comprise receiving, from a second user device and directed to the first edge device, a second request for virtual resources of the distributed computing cluster. The method may further comprise determining, by the first edge device, that a third edge device of the distributed computing cluster has been elected as the head node of the distributed computing cluster. The method may further comprise forwarding, by the first edge device to the third edge device, the second request, wherein forwarding the second request to the third edge device causes the second request to be processed by the distributed computing cluster.

In some embodiments, the first edge device exposes a public application programming interface accessible to the user device. The user device may access the remaining edge devices of the plurality of edge devices through the public application programming interface.

In some embodiments, an edge device is disclosed. The edge device may operate alone, or as part of a computing cluster of a plurality of edge devices. In some embodiments, the edge device comprises one or more processors and one or more (non-transitory) memories configured with computer-executable instructions that, when executed by the one or more processors, cause the edge device to perform the method disclosed above.

Some embodiments disclose a non-transitory computer-readable storage medium comprising computer-executable instructions that, when executed with one or more processors of an edge device (e.g., an edge device operating as part of a computing cluster of edge devices, cause the edge device to perform the method disclosed above.

DETAILED DESCRIPTION

Figure 1:
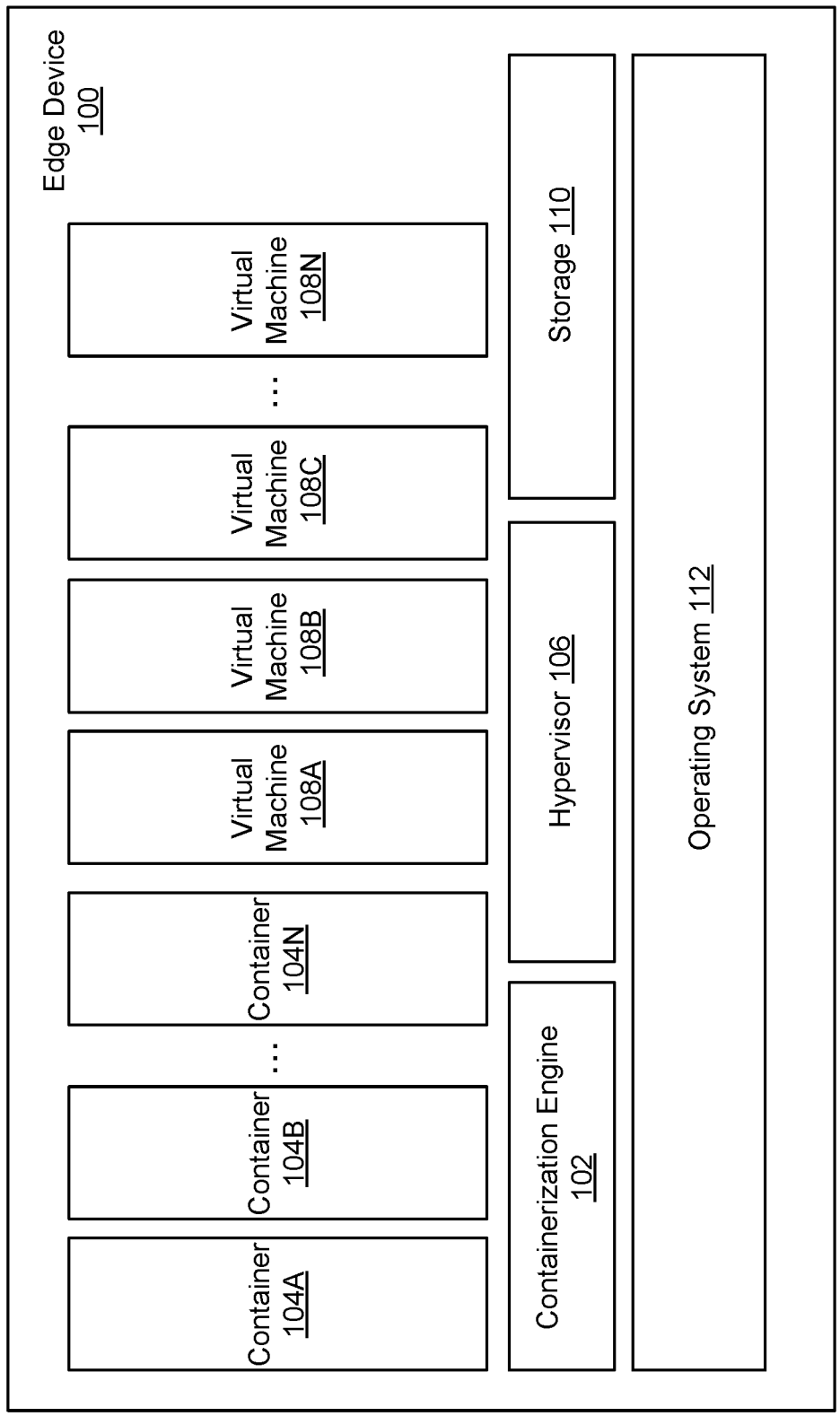
FIG. 1 is a block diagram of an example high-level architecture for a cloud infrastructure edge computing device, according to at least one embodiment.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Introduction

In some examples, a cloud-integrated edge service (e.g., implemented in an edge computing device, also referred to as "an edge device," for brevity) may be integral in addressing the desire to run time-sensitive cloud infrastructure application outside of a centralized data center (e.g., a datacenter of a cloud infrastructure service provider). Such an edge computing device may deliver computing and storage at the edge and/or in disconnected locations (e.g., remote locations separate from the centralized data center and lacking a public/private network connection (e.g., an Internet connection, a VPN connection, a dedicated connection, etc.) to enable low-latency processing at or near the point of data generation and ingestion. In some instances, a fleet of portable (which may be ruggedized for protection) server nodes (e.g., a fleet of edge devices) may be configured to physically bring the cloud infrastructure service to remote locations where cloud technology has been considered technologically infeasible or too cost prohibitive to implement.

To a customer (e.g., a user), the edge computing device can act as an extension of their cloud infrastructure: including virtual machines (VMs), containers, functions and data files, block volumes or object store services can also be delivered from the cloud infrastructure tenancy (e.g., a tenancy of the centralized cloud computing environment) with little to no modifications, and the customer experience may remain unchanged from that of the centralized cloud computing experience. Additionally, the edge computing device may be configured to implement both a control plane and a data plane that are part of a cloud infrastructure service provider. The data plane can be configured to manage data storage, migration, processing, etc., while the control plan can be configured for controlling the various services and architecture components of the computing device. Once the edge computing device is properly connected to a customer computing device (e.g., via a local area network (LAN)), the customer may be able to utilize the IaaS service (or at least a subset of it) using the same SDK and API used with the centralized cloud service.

The edge computing device can be delivered to a customer in a pre-configured form, such that the only action that might be required of the customer is to connect the nodes to a network (e.g., a local/on premise network that is accessible by a user computing device), power them up, and/or log in. The device can be pre-configured in various ways based on customer preference/request, or it can be in one of various configurations (e.g., storage-centric, compute-centric, etc.). The node or cluster of nodes can be portable and is intended to be mobile—when moved and set up again (or used while in motion), the deployment continues to run from where it turned off (or continuously). The edge computing device can also monitor for wide area network (WAN) connection availability (e.g., the Internet or the like), and can synchronize customer and management data with the cloud once connected to a WAN.

Some potential use cases for the edge computing device include: storage and processing, compute and input/output (I/O) intensive applications, machine learning, remote computing, low latency database and analytics, and data collection and migration. More specifically, the edge device can be used for storage and processing of large volumes of images, video, audio, and IoT sensor data generated in environments where WAN connection is latent or unavailable (e.g., in remote areas, an oil off-shore platform, or the like). Once this data is pre-processed, filtered, compressed, and/or secured it may be transported or transferred to the cloud service provider, where it can be further processed by the centralized server (e.g., traditional cloud service provider). The device can also be used for compute and I/O intensive applications, where low latency is paramount, such as tactical reconnaissance or 5G communications. The device can also be used for machine learning, with models trained in the cloud and running in disconnected locations to improve efficiency, intelligence, and/or productivity in manufacturing, document management, transportation, oil and gas mining, and/or telecommunications. It can also be used for remote computing requiring elevated security and airtight containment of data. Additionally, the device can be used for low latency database and analytics workloads, with more applications optimized over time. Further, the device can also be used for data collection and migration of large sets of object and database management system (DBMS) data into a cloud service provider, e.g., at faster speeds and lower cost than a WAN transfer.

The edge device can natively support distributed cloud paradigms, where complex, multi-stage compute workflows can be separated into individual components, which in turn can be deployed to the infrastructure of the edge device, on premise, and/or in the cloud. An example of such distributed workflow is represented in the following scenario. Massive amounts of data can be collected by an edge computing node deployed on an airplane (e.g., a military jet) in a reconnaissance operation with no Internet access (e.g., a disconnected edge computing device), where this data is be pre-processed in near real time by a machine learning model previously trained by the cloud service provider that provided the edge device. Even the first pass of processing the data with the models can detect significant anomalies and can alert personnel immediately—for example, a bridge may be destroyed and therefore the troops should be rerouted. When the airplane lands, the edge computing device can be physically connected to a network (e.g., an edge station potentially deployed at the airstrip). The pre-processed, filtered, smaller dataset can be loaded for final processing to a cluster of edge computing device nodes at the edge station. The original edge computing device can be released and can be loaded on another (or the same) airplane, for example to support the next mission. When processing at the edge station is complete, a 3D map update can be issued for immediate use. Change sets can then be uploaded by the edge station cluster to a datacenter and can be used to build future models providing intelligent tactical forecasts to the reconnaissance operation, or the like.

It should be appreciated that the following techniques may be employed in a variety of contexts such as telecommunications, oil and gas, healthcare, hospitality, agriculture, transportation, and logistics, and the like.

Embodiments described herein address these and other problems, individually and collectively. Specifically, embodiments of the present disclosure provide for a cloud infrastructure edge computing device.

Edge Device Architecture

An edge computing device (sometimes referred to as "a cloud-computing edge device," a "cloud infrastructure edge computing device," or an "edge device," for brevity), extends a user's centralized cloud computing tenancy by physically putting customer infrastructure and platform services where data is generated—on the edge, on premise, or completely disconnected. Each deployment is created to address specific customer needs by provisioning VM instance images and data from the customer's centralized cloud tenancy. These workloads remain fully functional offline as the edge device adapts to the connection state, operates in harsh environmental conditions, and is ready to sync with the cloud whenever the connection is re-established.

FIG. 1 is a block diagram of an example high-level architecture for a cloud infrastructure edge computing device (e.g., edge device 100), according to at least one embodiment. An overview of the software and hardware component of the edge device 100 is provided below.

In some examples, the edge device 100 may include containerization engine 102 (e.g., Docker, Kubernetes, etc.) configured to implement one or more containers (e.g., corresponding to container(s) 104A, 104B, 104C, to 104N, collectively referred to as "container(s) 104"). A containerization engine (e.g., the containerization engine 102) may be container-orchestration system for automating computer application deployment, scaling, and management. In some embodiments, the containerization engine may be configured to provide OS-level virtualization to deliver software in packages called containers. These containers can be isolated from one another and utilize respective software, libraries, and configuration files, and can communicate with each other through well-defined channels. In some embodiments, service(s) 104 may include any suitable number of services (e.g., one or more). These services may implement at least some portion of centralized cloud capabilities. Each service may be stand-alone or operate as a distributed cluster. The edge device 100 may further include a hypervisor 106 configured to implement one or more virtual machines (e.g., virtual machines 108A, 108B, 108C, to 108N, collectively referred to as "virtual machine(s) 108" or "VMs 108").

In some examples, the edge device 100 includes storage 110 (e.g., object and/or block storage for storing local data). The edge device 100 includes operating system (OS) 112. In some embodiments, the OS 112 may be optimized for executing on an edge device and/or specific to execution on an edge device. OS 112 may be configured to manage the hardware of edge device 100 and supports a data plane of the services running on the edge device 100. The OS 112 may be configured to support a specific deployment type (e.g., a single edge device deployment, or a specific edge device cluster configuration). The OS 112 may be configured to secure the edge device by disallowing or otherwise blocking direct access by customers.

In some embodiments, the edge device 100 may include hardware such as any suitable number of central processing units (CPUs) and/or storage drives. For example, the edge device 100 depicted in FIG. 1 may have one, two, or more CPUs, with various numbers of cores per processing unit, and it may include any number of storage drives (e.g., 6.4 terabyte (TB) drives, or the like). As a non-limiting example, the edge device 100 may include block and/or object storage of any suitable size. The edge device 100 may include any suitable number of central processing units (CPUs), graphics processing units (GPUs), random access memory (RAM) of any suitable size, one or more ports (e.g., QSFP28, RJ45, dual ports, etc.), tamper-evident seals, or any suitable combination of the above components.

In some examples, the basic system functionality/services can be accessed via RESTful APIs have a custom load of software based on Linux. The virtual machine(s) 108 may individually be a Kernel-based Virtual Machines (KVM) (e.g., a virtual machine managed by a virtualization module in the Linux kernel that allows the kernel to function as a hypervisor) and/or a hardware-based Virtual Machine (e.g., a virtual machine managed by a virtualizer, such as Quick EMUlator (QEMU), that can perform hardware virtualization to enable virtual machines to emulate of number of hardware architectures). Although storage 110 is represented as a separate component from the service(s) 104 and VM(s) 108, it can run as a container (e.g., container 104A) or in a VM (e.g., VM 108A). In some examples, it may be favorable to implement the storage 110 (e.g., object storage, block storage, etc.) as a container.

Figure 2:
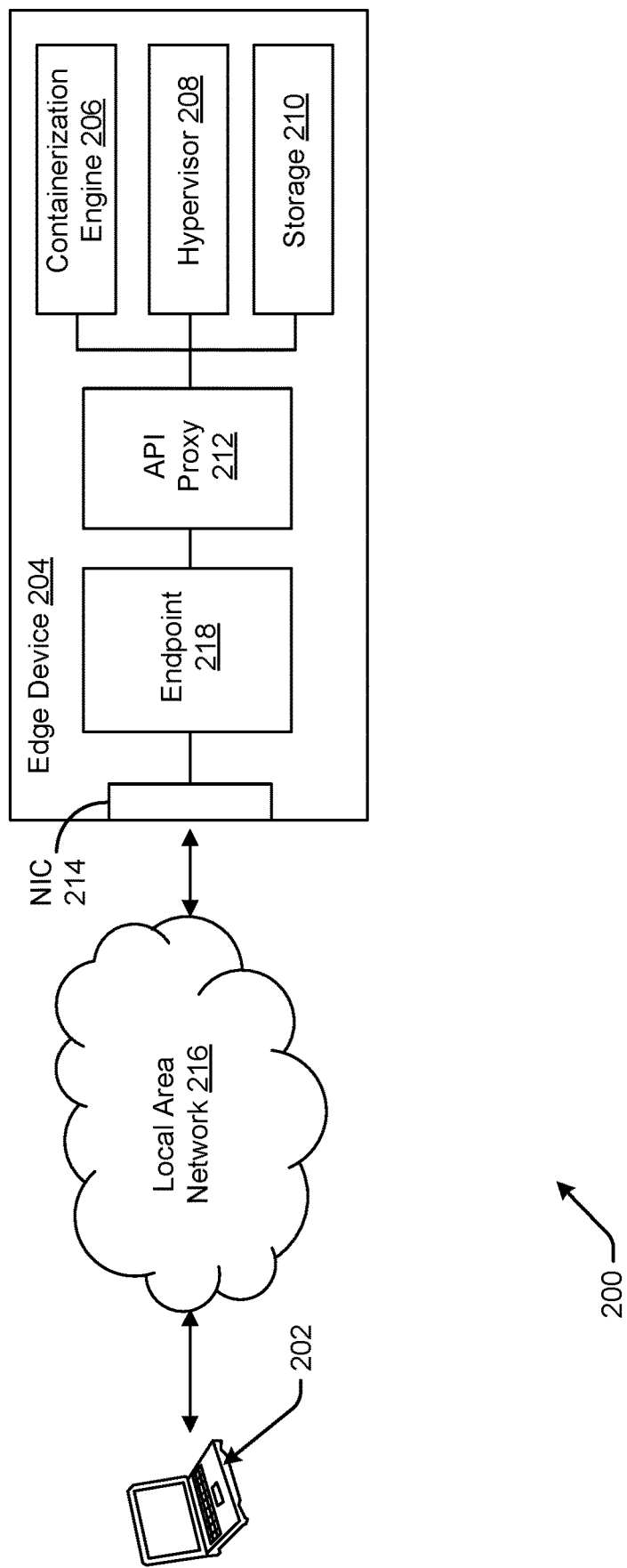
FIG. 2 is a block diagram of an example architecture for connecting a user computing device to a cloud infrastructure edge computing device, according to at least one embodiment.

FIG. 2 depicts an example architecture 200 for connecting the edge device described herein (e.g., edge device 100 from FIG. 1) to a computing device 202 (e.g., a user computing device). The computing device 202 can be any type of computing device including, but not limited to, a laptop computer, a desktop computer, or the like. The edge device 204 (an example of the edge device 100 of FIG. 1) may include containerization engine 206 (an example of the containerization engine 102 of FIG. 1), hypervisor 208 (an example of the hypervisor 106 of FIG. 1), and storage 210 (an example of the storage 110 of FIG. 1).

Additionally, as mentioned briefly above, the edge device 100 may include an API proxy 212 for managing the RESTful API calls received from the computing device 202. The API calls may enter the edge device 204 via network interface card (NIC) 214 that is internal to the edge device 204. The NIC 214 may be used to connect the edge device 204 to the computing device 202 via a local area network (e.g., the LAN 216). The API calls received by the NIC 214 may be transmitted to an exposed endpoint that may implement a Web server (e.g., endpoint 218). The web server can transmit the requests to the API proxy 212, which can route the requests to the appropriate service (e.g., containerization engine 206, hypervisor 208, and/or storage 210). The exposed endpoint/web server may also be configured to implement the lightweight console that is for use by the customer (e.g., the user interface displayed on the computing device 202).

The lightweight console can run within a web browser (e.g., Mozilla Firefox, or the like) on a laptop computer, desktop computer, or other network-accessible device (e.g., connected to the local area network (LAN 216)) that is network-connected to the edge device 204 (e.g., via a router, cable, etc.). The edge device 204 can expose the endpoint 218 for the console connection, and the web server can transmit data to the web browser of the computing device 202 over the LAN 216.

Figure 3:
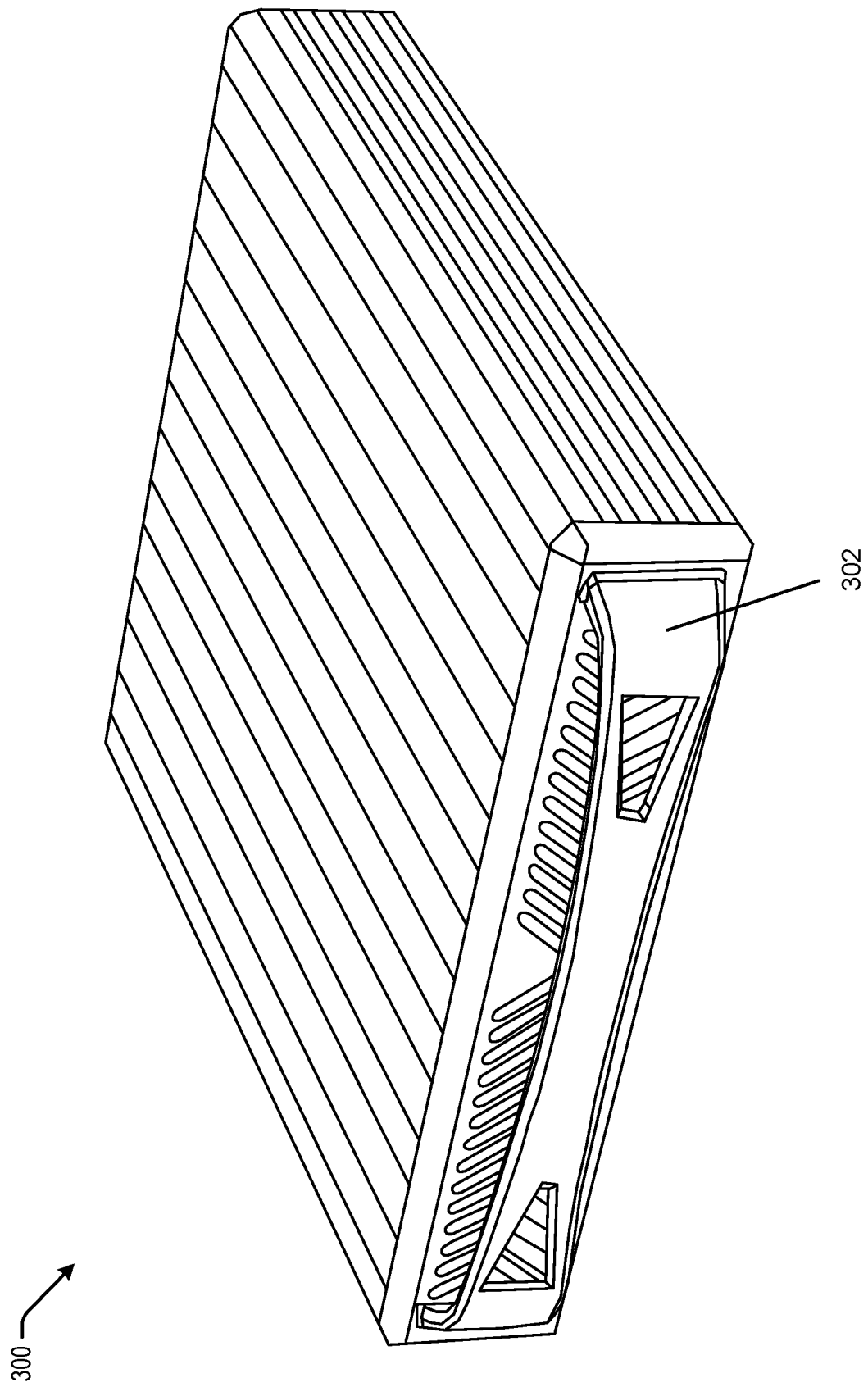
FIG. 3 is a block diagram of an example enclosure for a cloud infrastructure edge computing device, according to at least one embodiment.

FIG. 3 illustrates an example physical enclosure 300 of the edge device described herein (e.g., edge device 100 from FIG. 1). Various different form factors, shapes, colors, etc., can be employed to build a box (e.g., ruggedized) that can house the edge computing device. The physical enclosure can include handle 302, as shown, and may include tamper evident elements, so that if anyone breaks the enclosure open, it will be evident. In this way, the service provider that provides the edge computing device can ensure that the device is not modified. In some examples, the physical enclosure 300 may not be possible to open. However, in some cases, it might be possible, but it would require extreme measures.

Figure 4:
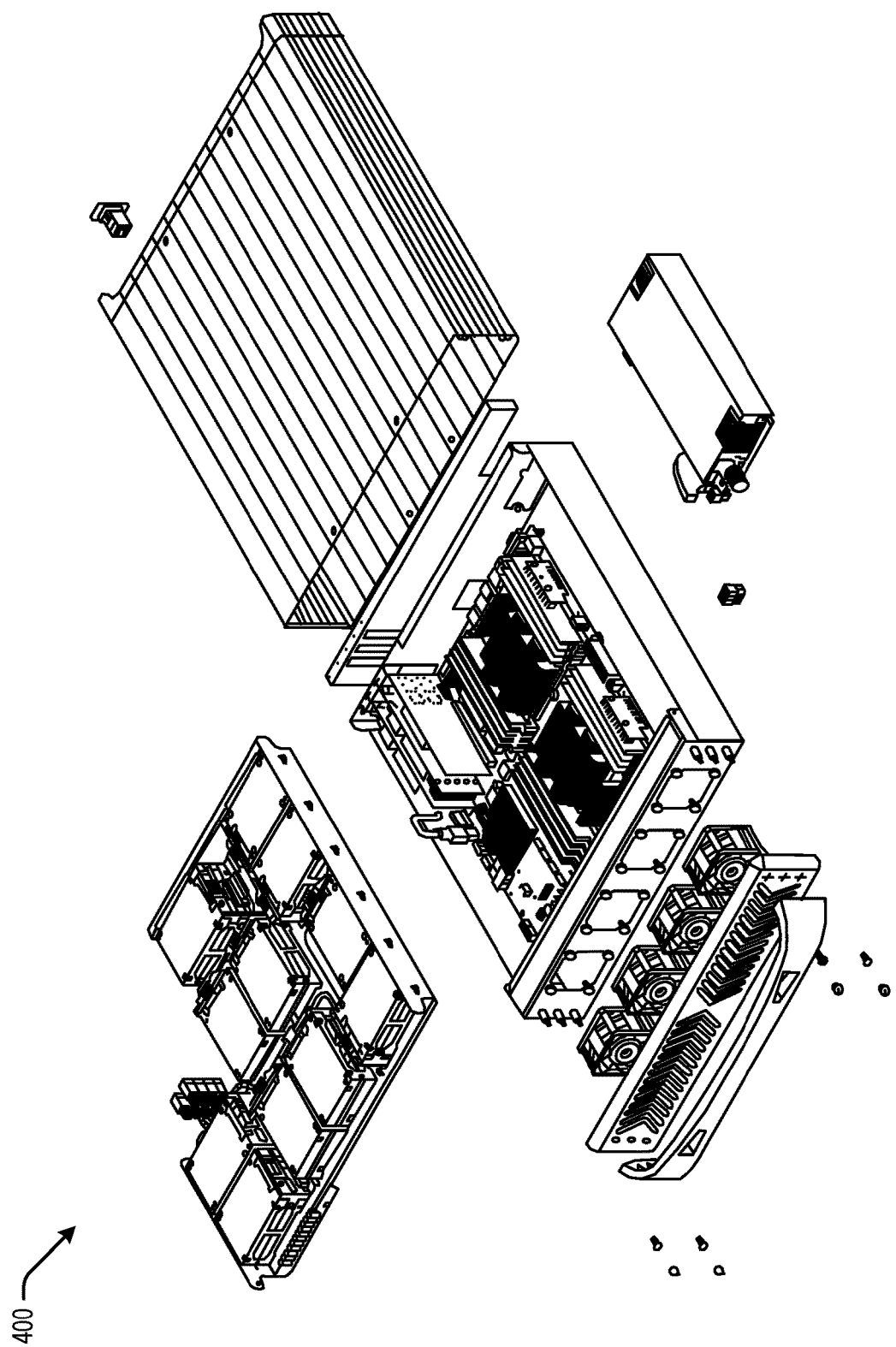
FIG. 4 illustrates an exploded view of the cloud infrastructure edge computing device described herein, in accordance with at least one embodiment.

FIG. 4 illustrates an exploded view of the cloud infrastructure edge computing device described herein (e.g., edge device 400, an example of the edge device 100 of FIG. 1), in accordance with at least one embodiment. The various components described with respect to FIGS. 1 and 2 can be communicatively attached to one or more motherboards and/or interface cards within the edge device 400. The illustrated configuration of components is but just one implementation. The specific locations of components shown is not intended to be limiting, and as noted, any configuration that is capable of implementing the functionality described herein is acceptable. Once the components are installed, the entire box can be closed, sealed, and locked with tamper-evident components.

The edge device 400 is a single enclosure. The enclosure may be designed to house any suitable number of serially attached SCSI (SAS) solid-state drives (SSDs) and all other components (e.g., CPU, memory, GPU, etc.) within the enclosure. The system may include one or more (e.g., 12 Gb) SAS connections to each drive in a fully contained sheet metal enclosure designed to fit within a standard 19" rack resting on an L bracket/shelf, on a table top or upright next to a desk with the use of a floor stand.

The system may include a tamper evident enclosure, front security plugs covering screws holding a front bezel in place with rear security interlock features. In some embodiments, the system may include a dual socket motherboard and any suitable amount of DRAM. In some embodiments, the system may include any suitable number (e.g., 2, 3, etc.) SATA SSDs, storage controllers, embedded network connections, one or more ports (e.g., dual ports, serial ports, etc.), one or more fans as part of a cooling system, or any suitable combination of the above.

As a non-limiting example, the edge device 400 may be made up of an external extruded aluminum case secured in the front with a vented bezel and rear panel only exposing I/O connections required for data transfer and management. Mounting can be designed to mount the any suitable motherboard, fans, and power supply.

Figure 5:
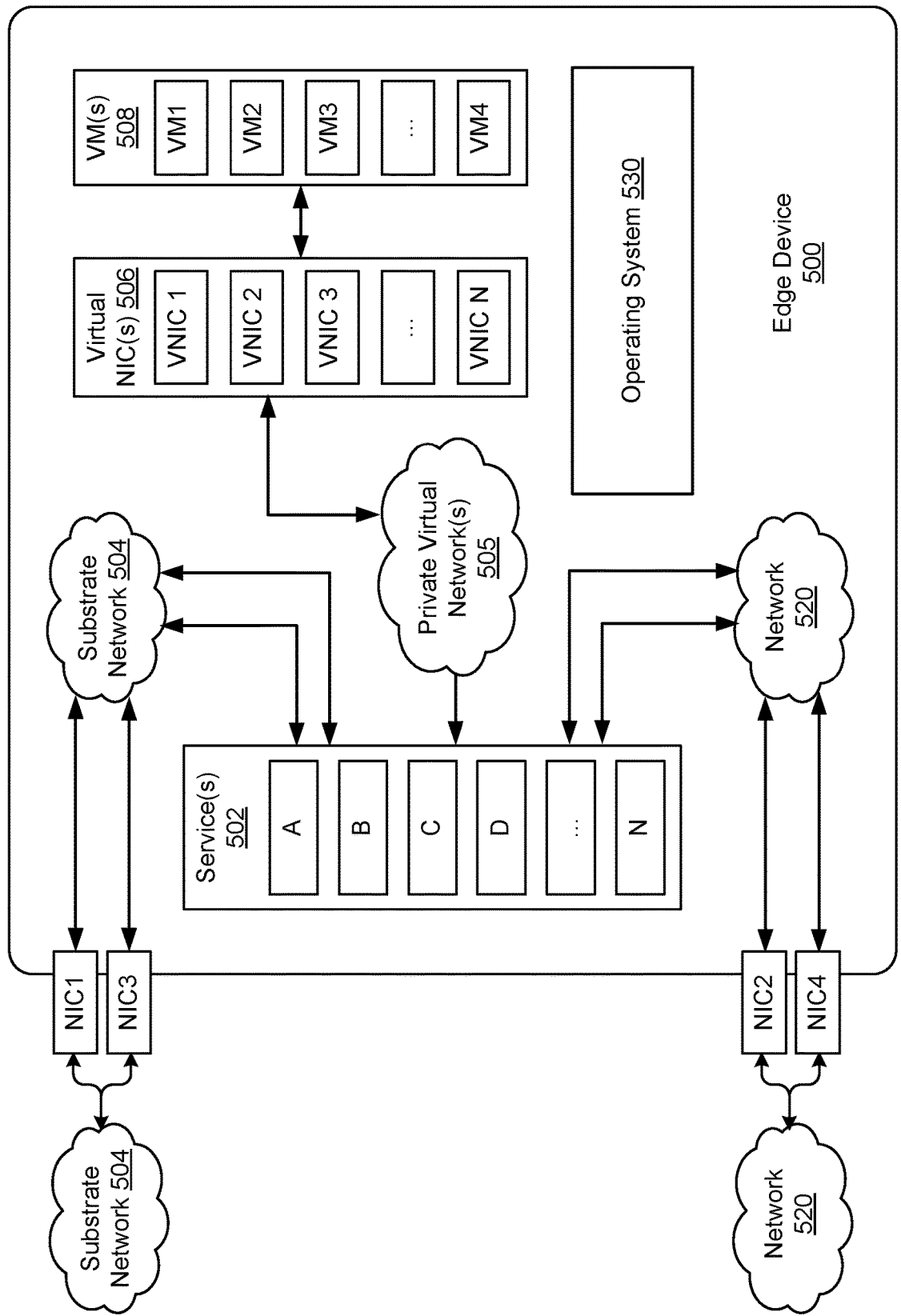
FIG. 5 is a block diagram of an example computer architecture of a cloud infrastructure edge computing device, according to at least one embodiment.

FIG. 5 is a block diagram of an example computer architecture of a cloud infrastructure edge computing device (e.g., edge device 500, an example of the edge devices 100 and 204, of FIGS. 1 and 2, respectively), according to at least one embodiment. The edge device 500 can be thought of as a cloud-integrated service that extends some or all of conventional cloud capabilities to locations that may not be accessible by or have access to cloud data centers. This can be achieved via portable ruggedized server nodes that provide cloud-like functionality in locations with no WAN connectivity. This allows customers to shift select cloud workloads to remote locations and enable intensive data processing operations close to the data ingestion points at the edge of their cloud infrastructure.

The edge device 500 may include any suitable number of services (e.g., service(s) 502). Each service may run as a container (e.g., a Docker container) locally on the edge device 500. The service(s) 502 may be communicatively connected via a substrate network 504 such that the communications between services are encrypted (e.g., in accordance with a security protocol such as MACsec). Each container may be assigned a substrate IP address (e.g., a static address) with which traffic can be addressed. In some embodiments, a security protocol (e.g., MACsec) is configured at provisioning time (e.g., before the edge device 500 is shipped to the user). The edge device's system software (including service(s) 502) may execute in the secure environments protected by boot security software (e.g., Trenchboot Secure Launch). Users may be restricted from accessing the secure environment and/or the substrate network 504. To minimize the amount of resources used by these services, the service code may be compiled and saved to disk to decrease RAM space as well as decrease the CPU load on the edge device 500.

Some example services included in service(s) 502 may include a UI console service, an identity control plane (CP) service, an identity data plane (DP) service, a compute application programming interface (API) service, a compute worker thread service, a virtual network (VN) API service, a block storage API service, a function-as-a-service service, an events service, an object storage management service (e.g., implementing a storage platform such as Ceph Storage or the like), a compute DP service (e.g., an example of hypervisor 208 of FIG. 2), a VN DP service, a block storage management service, a function-as-a-service API service, a function-as-a-service load balancing (LB) service, a function-as-a-service process thread service, a distributed data store management service (e.g., etcd3), a dynamic host configuration protocol service, a domain name system service, a network time protocol (NTP) service, to name a few. Some example functionality provided by these services is discussed below.

By way of example, compute DP service may be configured (e.g., preconfigured and provisioned onto the edge device 500) to isolate the VM(s) 508 on the same hypervisor host. The compute DP service can utilize any suitable container engine (e.g., Docker container, MicroContainer, or the like) to isolate the VM(s) 508 on the same hypervisor host from each other. The compute DP service may utilize any suitable hypervisor (e.g., Quick EMUlator (QEMU), Kernel-based Virtual Machine (KVM), etc.) to provide virtual hardware emulation for VM(s) 508. In some embodiments, VNIC(s) 506 are attached to subnets of any suitable number of virtual networks (e.g., private virtual network(s) (PVN(s))) 505 and are assigned private Internet Protocol (IP) addresses. One VM may have multiple VNICs from different VCNs and different subnets. The maximum number of VNICs can be limited by predefined thresholds (e.g., configuration data referred to as "VM shape" that defines VNICs per VM count, VNIC shape, etc.). In some embodiments, the predefined thresholds are applied to each of the VM(s) 508. The subnets utilized by the VNIC(s) 506 may be isolated by VLANs. In some embodiments, some or all of the VNIC(s) 506 may be assigned public and/or private IP addresses. A public IP address is an address in the network 520, while a private IP address refers to an IP address of the PVN(s) 505.

In some embodiments, the edge device 500 implements various networking functionality via a number of services such as a network address translation (NAT) service, a dynamic host configuration protocol (DHCP) service, a domain name system (DNS) service, a network time protocol (NTP) service, a metadata service, and a public API service). The metadata service may provide initialization data and other metadata to all VM(s) 508. In some embodiments, DHCP service assigns private IP addresses to each of the VNIC(s) 506, each of the VM(s) 508 having one or more VNICS. DNS service may provide domain name resolution to VM(s) 508 on the edge device 500. NTP may provide time synchronization to VM(s) 508. In some embodiments, a public IP service executing as part of service(s) 502 may enable a VM to access a public API without assigning the VM a public IP and without configuring a service gateway.

In some embodiments, at least one of the VM(s) 508 may implement block (or object) storage. In some embodiments, the hypervisor associated with a virtual machine may include a library that enables the hypervisor to use a distributed data storage platform (e.g., Ceph). The library may utilize a protocol associated with that storage platform (e.g., RADOS Block Device (RBD) to facilitate storage of block-based data. The distributed data storage platform may be implemented over multiple virtual machines. In some embodiments, the distributed data storage platform supports making snap shots and copying block volumes. VM images and VM block volumes can be Ceph block devices. In some embodiments, the VM(s) implementing the distributed data storage platform will use system-reserved resources (e.g., eight CPU cores, or any subset of the total number of CPUs available on the edge device 500). For example in order to provision a boot volume, a block device image may be copied to a boot volume of the block device. The distributed data storage platform may use block devices that include multiple nodes for redundancy. If some node fails then the block device can continue to operate. In some embodiments, the distributed data storage platform (e.g., Ceph or the like), automatically recovers the block device data in case of a few node failures. Block storage may be utilized to store images for any suitable deployable resource. By way of example, an image may be utilized for launching VMs. In some embodiments, the image may correspond to a particular VM shape (e.g., a compute heavy VM, a GPU optimized VM, a storage VM, and the like).

Compute API service may support the following operations: 1) VM launch and terminate, 2) VM stop, start, reboot, 3) List VMs and/or get information on a specific VM, 4) obtain VM console history API, 5) obtain a VM snap shot, 6) attach/detach block volumes, and the like. In some embodiments, Compute API service can be used to call other services (e.g., compute DP service, identity DP service for authentication and authorization, etc.).

Some of the functionality of other services will be discussed in connection with FIG. 7. In general, although each service may not be discussed in detail herein, the general functionality provided by the service(s) 502 may include the functionality of cloud services provided by a remote cloud service provider. In some embodiments, the edge device 500 may be associated with a predefined region and/or realm such that some of the service(s) 502 may operate as if they were operating in a cloud computing environment, despite the fact they are operating on one or more local device(s) (one or more edge devices) as a single instance or as part of a distributed service that may have no or intermittent public network access to a cloud computing environment associated with the customer. A "region" refers to a geographic location at which a service center resides. A "realm" refers to a logical collection of regions. Realms may be isolated from each other and do not share data.

In some embodiments, the edge device 500 may provide any suitable number of virtual networks (e.g., PVN(s) 505) using compute, memory, and networking resources (e.g., virtual network interface card(s) (VNIC(s) 506)). A virtual network is a logical network that runs on top of a physical substrate network. Using the service(s) 502, one or more customer resources or workloads, such as virtual machines (e.g., virtual machine(s) (VM(s)) 508, executing a compute instance) can be deployed on these private virtual networks. Any suitable combination of VM(s) 508 can execute functionality (e.g., a compute instance, storage, etc.) which is individually accessible through a virtual NIC (e.g., one of the virtual NIC(s) 506). Each VM that is part of a PVN is associated with a VNIC that enables the VM (e.g., a compute instance) to become a member of a subnet of the PVN. The VNIC associated with a VM facilitates the communication of packets or frames to and from the VM. A VNIC can be associated with a VM when the VM is created. PVN(s) 505 can take on many forms, including peer-to-peer networks, IP networks, and others. In some embodiments, substrate network traffic of the service(s) 502 may be encrypted and/or isolated (e.g., by virtue of different PVNs or subnets) from network traffic of one or more the VM(s) 508 executing on the edge device 500.

The edge device 500 thus provides infrastructure and a set of complementary services that enable customers to build and run a wide range of applications (e.g., compute instances), services, and/or storage in a highly available, physically local, and virtual hosted environment. The customer does not manage or control the underlying physical resources provided by the edge device 500 but has control over expanding or reducing virtual machines (e.g., compute instances, virtual NICs, block or object storage, etc.), deploying applications to those virtual machines, and the like. All workloads on the edge device 500 may be split into different CPU sets (e.g., VM and non-VM). One set (e.g., non-VM such as workloads performed by the service(s) 502) may utilize a subset of CPU cores (e.g., 8) of the edge device 500, while the other set (e.g., VM workloads performed by the VM(s) 508) may utilize a different subset of CPU cores.

The edge device 500 may be communicatively connected to a user device (e.g., the computing device 202 of FIG. 2) via one or more network interfaces (e.g., NIC2 and/or NIC 4) and network 520 to interact and/or manage the VM(s) 508. In certain embodiments, a lightweight console can be provided at the user device via a web-based user interface that can be used to access and manage the edge device 500. In some implementations, the console is a web-based application (e.g., one of the service(s) 502) provided by the edge device 500.

FIG. 5 depicts a single edge device. However, it should be appreciated that more than one edge device may be utilized as a distributed computing cluster.

Figure 6:
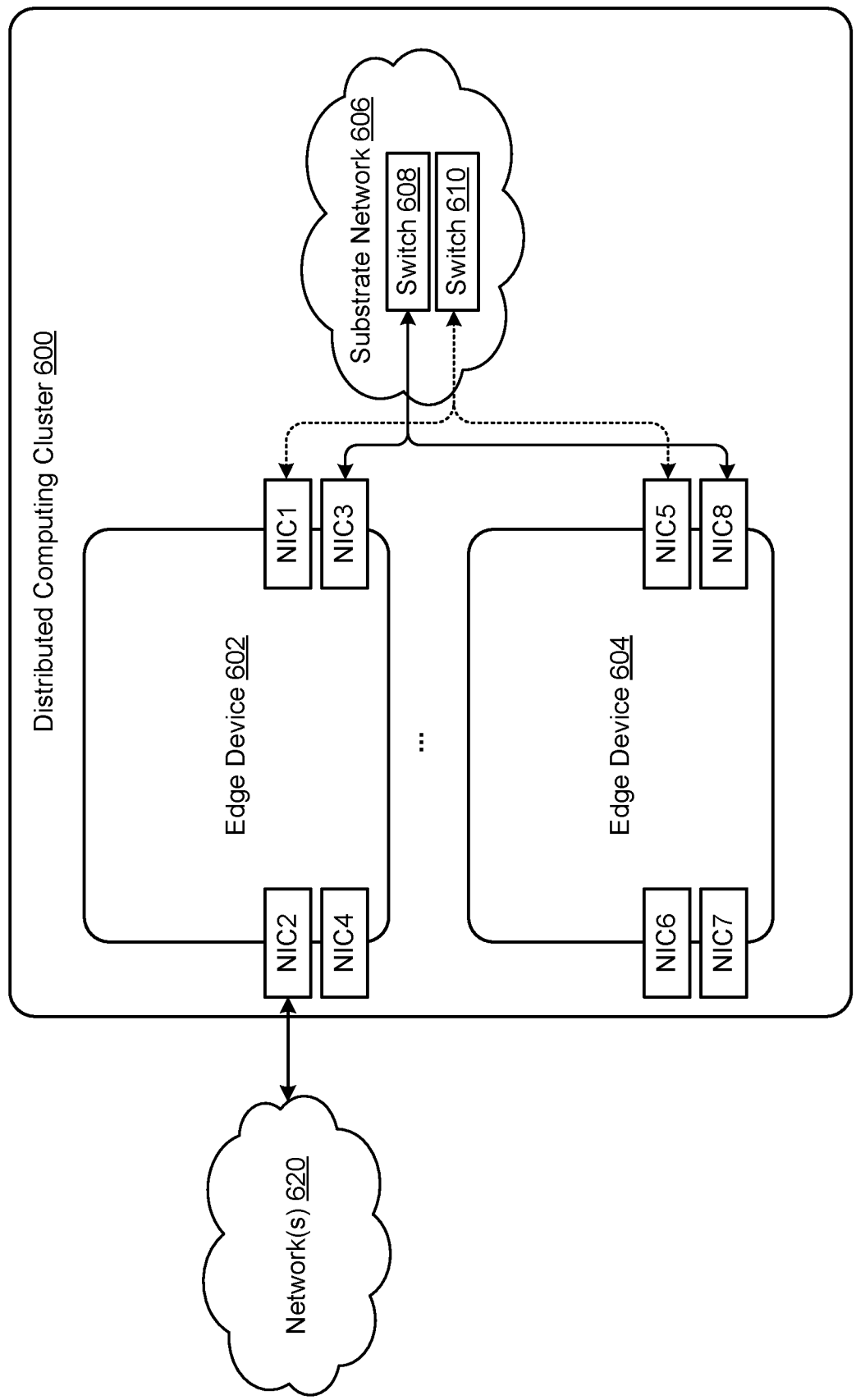
FIG. 6 is a block diagram depicting a distributed computing cluster that includes one or more edge computing devices, according to at least one embodiment.

FIG. 6 is a block diagram depicting a distributed computing cluster 600 that includes one or more edge computing devices (e.g., edge device 602 and 604, each an example of the edge device 500 of FIG. 5), according to at least one embodiment.

Each edge device of the distributed computing cluster 600 may be connected via substrate network 606 (an example of the substrate network 504 of FIG. 5. In some embodiments, the edge devices of the distributed computing cluster 600 (sometimes referred to as "edge computing nodes" or "edge nodes") may be connected by the substrate network 606 using one or more switches (e.g., switch 608 and/or 610). In some embodiments, NIC1 and NIC5 may include a particular connector (e.g., RJ45 connector) while NIC3 and NIC8 may include the same or a different connector (e.g., a QSFP28 100 GbE connector). In some embodiments, only one edge device of the distributed computing cluster 600 is connected to a customer network such as network(s) 620 (an example of the network 520 of FIG. 5). Thus, not only may traffic between services of an edge device be encrypted and isolated from other traffic of a given edge device, but traffic between distributed services operating across multiple edge devices may also be encrypted and isolated from other traffic of the computing cluster. In some embodiments, each edge device is preconfigured as a particular node in the distributed computing cluster 600. In other embodiments, the user can configured the number and topology of the edge devices of the distributed computing cluster 600.

Figure 7:
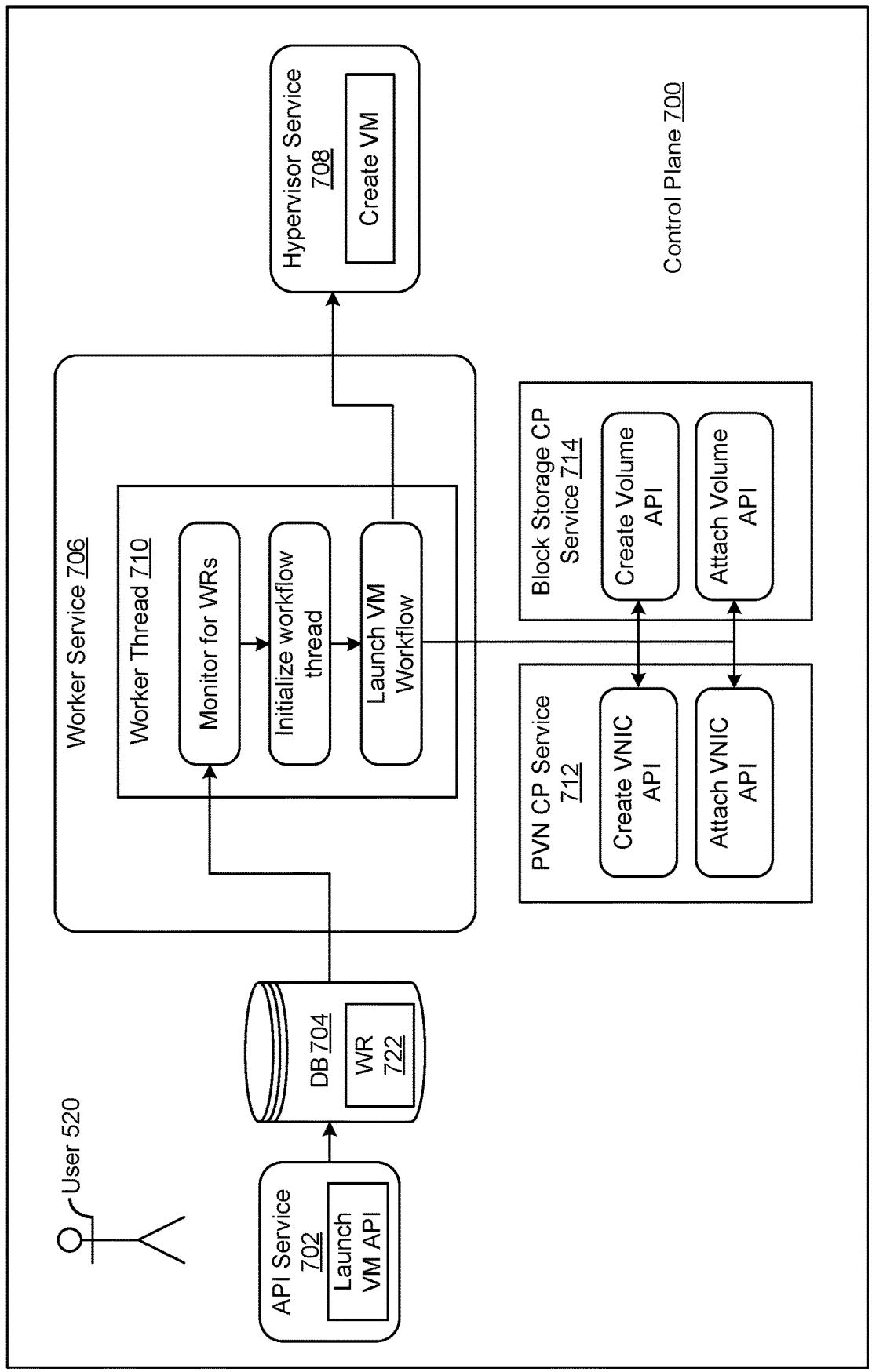
FIG. 7 is a block diagram depicting a control plane and flow for executing a workflow by one or more components of a cloud infrastructure edge computing device, according to at least one embodiment.

FIG. 7 is a block diagram depicting a flow 700 for executing a workflow by one or more components of a cloud infrastructure edge computing device, according to at least one embodiment. Components that execute the flow 700 may include API service 702, database (DB) 704, worker service 706, hypervisor service 708, PVN CP service, Block storage CP service 714, although more or fewer services may be included. In some embodiments, each of the services of FIG. 7 are an example of a service of the service(s) 502 of FIG. 5. In some embodiments, at least some of the functionality discussed in connection with the services of FIG. 7 may be combined in any suitable combination and provided as a single service or instances of the same service. By way of example, in some embodiments, the functionality of services 702-708 may be provided by a single service (e.g., compute CP service discussed above in connection with FIG. 5). In some embodiments, the functionality provided by the services 702-708 may be provided by a single edge device (e.g., edge device 500 of FIG. 5) or by two or more edge devices (e.g., by edge device 602 and edge device 604 of FIG. 6).

In some embodiments, the API service 702 may be configured to accept work requests that include intended state data that describes an intended state of a set of data plane resources (e.g., VM(s) 508 of FIG. 5). As a non-limiting example, user 720 may utilize a user device (e.g., the user device *202 of FIG. *2) to access a user interface with which he can make various selections indicating a desire to launch a VM. The user input may be received by the API service 702 (an example of the compute CP service of FIG. 5) which may generate a work request (WR) (e.g., WR 722) and utilize a predefined Launch VM API to store the work request in a distributed database (e.g., DB 704). In some embodiments, the DB 704 may be a computing cluster, which is configured to use etcd3 as an immediately consistent, highly-available, transactional, distributed database. Generally, a work request indicates a desire and information needed to create and/or modify data plane resources such as VM(s) 508. In some embodiments, the work request includes state information indicating a desired state for the data plane resource. In some embodiments, the DB 704 may be accessible to all services operating on any edge device (and by services operating on any suitable edge device of an edge device cluster such as distributed computing cluster 600).

Worker service 706 (e.g., an example of the compute CP service of FIG. 5) may be configured to execute one or more worker processes (e.g., one or more computing threads, such as computing thread 710). Some of these worker processes may be configured by the worker service 706 at any suitable time to execute a continuous and/or ongoing predefined workflow. By way of example, the worker service 706 may configure one or more worker threads (e.g., including computing thread 710) to monitor the DB 704 for new work requests (e.g., WR 722). The computing thread may be configured to determine if a work request WR 722 is already being attended to. In some embodiments, this entails checking a predefined storage bucket within DB 704 for a unique identifier associated with WR 722. If the unique ID included within WR 722 does not appear in the bucket (or the WR is otherwise indicated as having not been picked up for processing), the computing thread 710 (e.g., a nanny thread) may initialize a workflow thread (e.g., another instance of a computing thread 710) which may then be configured by the computing thread 710 to execute a workflow corresponding to launching a VM corresponding to the WR 722.

The initialized workflow thread may be communicatively coupled (e.g., via the substrate network 504 of FIG. 5) to a workflow service (not depicted). The workflow service may be configured to identify, from one or more predefined workflows, a predefined workflow that corresponds to launching a VM, and therefore, to the WR 722. These predefined workflows identify one or more steps/operations to be taken, and a sequence to those steps, in order to achieve a predefined goal (e.g., launching a virtual machine, stopping/starting a virtual machine, terminating a virtual machine, creating a block volume, removing a block volume, etc.). The workflow thread may launch the VM workflow and oversee its execution by various other entities. In some embodiments, the workflow thread may pass any suitable portion of the intended state data of the DP resource to any suitable combination of services.

As a non-limiting example, as part of the workflow for launching a virtual machine (e.g., a VM to be hosted by hypervisor service 708), one or more APIs can be called for creating and attaching the VNIC. Similarly, a number of APIs may be provided for creating and/or attaching a block storage volume API. In some embodiments, the workflow thread may perform any suitable call to one or more APIs to invoke the functionality of PVN CP Service 712, which in turn may be configured to create and attach a VNIC. The workflow thread may then call block storage CP service 714 which may then execute any suitable operations to create and attach a block storage volume. The worker thread overseeing the workflow may ensure a designated order (e.g., create the VNIC first before creating the block volume). This worker thread may be configured to catch any errors and/or exceptions from one or more services it has invoked. If no exceptions/errors are encountered, the worker thread overseeing the workflow can provide any suitable data to the hypervisor service 708 (via the substrate network), which in turn, execute functionality for creating the VM requested. The hypervisor service 708 may provide actual state data for the newly launched VM. In some embodiments, the worker thread overseeing the workflow can store the actual state data in the DB 704 for later reference (e.g., when a monitor may determine whether the actual state data matches the requested state data indicating no changes needed or when the actual state data fails to match the requested state data, indicating a change of the data plane resources is needed).

In some embodiments, the workflow thread may be communicatively coupled to a cluster manager (not depicted). Cluster manager may be configured to manage any suitable number of computing clusters. In some embodiments, the cluster manager may be configured to manage any suitable type of computing cluster (e.g., a Kubernetes cluster, a set of computing nodes used to execute containerized applications, etc.). The workflow thread may be configured to execute any suitable operations to cause the cluster manager to execute any suitable orchestration operation on the DP resource(s) (e.g., a VM) in accordance with the instructions identified to bring the DP resource(s) in line with the intended state data. In some embodiments, a monitoring entity (e.g., the workflow thread, a thread launched by the workflow thread) may be communicatively coupled to DP resource(s) 116 and configured to monitor the health of DP resource(s). In some embodiments, the monitoring entity may be configured to store any suitable health data in the DB 704.

The specific operations and services discussed in connection with FIG. 7 is illustrative in nature and is not intended to limit the scope of this disclosure. The particular operations performed and services utilized may vary depending on the particular workflow associated with the requested operations.

Figure 8:
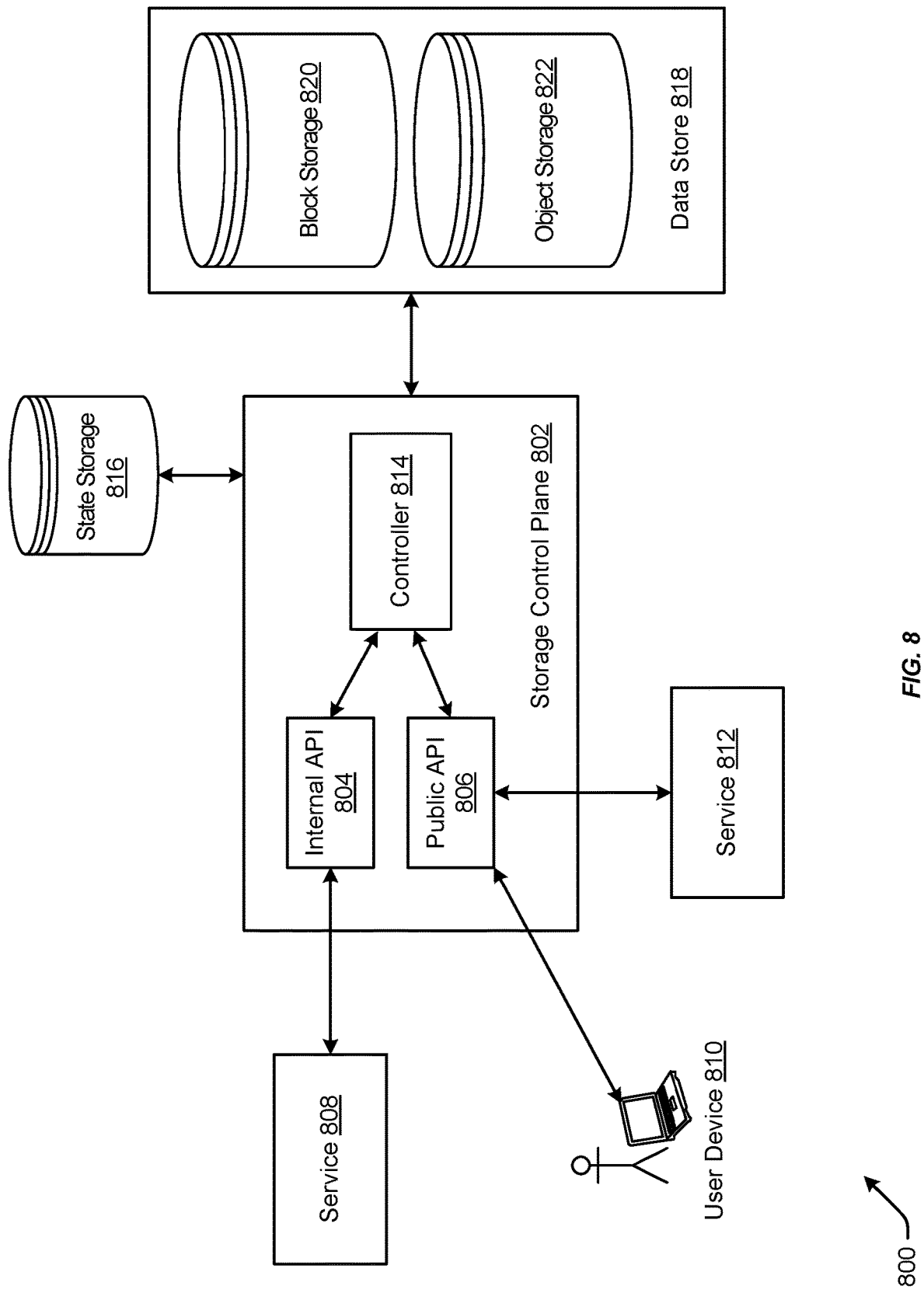
FIG. 8 is a block diagram depicting a storage system provided by an edge device, according to at least one embodiment.

FIG. 8 is a block diagram depicting a storage system 800 provided by a single edge device, according to at least one embodiment. Storage system 800 may include storage control plane 802. Storage control plane 802 may be configured to expose internal API 804 and public API 806. Internal API 804 may be utilized by onboard services (e.g., service 808, an example of the service(s) 502 of FIG. 5) to invoke the functionality of storage control plane 802. In some embodiments, public API 806 may be utilized by a user device 810 and/or service 812 (an example of the service(s) 502). In some embodiments, storage control plane 802 may be an example of the service(s) 502 and may be communicatively connected to service 808 and service 812 via a private network (e.g., substrate network 504 of FIG. 5). Storage control plane 802 may be communicatively connected to user device 810 via a public network (e.g., network 520 of FIG. 5).

In at least one embodiment, storage control plane (CP) 802 includes controller 814. Controller 814 may be configured to communicate with state storage 816 (an example of the database 704 of FIG. 7) and data store 818. State storage 816 may be implemented by a computing cluster, which is configured to utilize a distributed key-value store (e.g., etcd3) an immediately consistent, highly-available, transactional, distributed database. State storage 816 may be configured to store any suitable state information indicating a desired state for one or more data plane resources, a current/actual state for one or more data plane resources, work requests, or any suitable data related to one or more data plane resources (e.g., VNIC(s) 506, VM(s) 508, etc.).

The edge device on which storage system 800 executes may be one edge device of a computing cluster. If the computing cluster (referred to herein as an "edge device cluster") includes more than a threshold number of devices (e.g., seven), the edge device cluster may be configured to enable only the threshold number of devices to execute respective instances of state storage 816.

In some embodiments, service 808 may be a compute control plane service of the service(s) 502 of FIG. 5. The service 808 may be configured to manage compute resources such as boot volumes, block volumes, virtual machines, virtual network devices (e.g., a virtual network interface card), or the like. In some embodiments, service 808 may be configured to perform any suitable combination of the following actions: 1) Create/Delete/Get Boot Volume 2) Attach/Detach Volume, 3) Attach/Detach Boot Volume.

As another example, service 808 may be an API service (e.g., API service 702 of FIG. 7), an example of the service(s) 502 of FIG. 5. The service 808 may be configured to receive work requests related to creating, deleting, and/or modifying data plane resources. In some embodiments, service 808 may invoke the functionality of storage control plane 802 to store a received work request in state storage 816 for subsequent processing as described above in connection with FIG. 7. In some embodiments, the service 812 may be an identity service configured to authenticate and/or authorize users to perform various operations. Any suitable combination of the services 808 and 812 may be communicatively connected with the storage control plane 802 via internal API 804 and/or public API 806. As pictured, service 808 is connected via internal API 804 and service 812 is connected via public API 806. However, user device 810 may be restricted to access storage control plane 802 via public API 806. Internal API 804 and/or public API 806 may be components of the storage control plane 802 or separate services of the service(s) 502 of FIG. 5.

Controller 814 may be configured to manage data store 818. Data store 818 may include block storage 820 and/or object storage 822. Although not depicted in FIG. 8, data store 818 may additionally include a file storage system or any suitable combination of block storage 820, object storage 822, and the file storage system. In some embodiments, any suitable combination of block storage 820 and/or object storage 822 may be encrypted. By way of example, block storage 820 and/or object storage 822 may be encrypted with Advanced Encryption Standard (AES) algorithm using 236-bit encryption.

In some embodiments, volumes within block storage 820 may be a predefined size (e.g., 300 gigabytes (GB)) by default. Similarly, boot volumes may be the same or a different predefined size (e.g., 50 GB) by default. In some embodiments, users may be provided options via user device 810 to create block volumes in sizes within a predefined range (e.g., 50 GB to 6 terabytes (TB)) and potential in a predefined size increment (e.g., in 1 GB increment). In some embodiments, users may attach up to a maximum number (e.g., 32, 64, etc.) number of volumes per instance. In some embodiments, the block storage 820 may be configured to provide nearly 100% (99.99%) annual durability for block and boot volumes.

Users (and/or any suitable combination of the service(s) 502) may request various operations be performed such as creating a volume, deleting a volume, obtaining data associated with a volume, updating a volume, and listing a number of volumes (e.g., the volumes of block storage 820). Users (and/or any suitable combination of the service(s) 502) may request similar operations with respect to objects of the object storage 822 such as creating, deleting, obtaining, updating, and/or listing an object. In some embodiments, users may utilize the interfaces of user device 810 to request a full backup of one or more boot volume(s), block volume(s), and/or object(s) on demand. Likewise, users may restore a backup of a volume to a new volume. In some embodiments, a user may increase or decrease the size of the block storage 820 and/or any suitable number of boot and/or block (data) volumes. User input and/or data provided by the user device 810 may be transmitted to and/or received from the controller 814 via public API 806.

As a non-limiting example, a user may utilize interfaces provided at the user device 810 to request a new volume. The request may be transmitted via public API 806 and received by the controller 814. In some embodiments, controller 814 may invoke authentication/authorization functionality of service 812 based on sending a request to service 812 via public API 806. Service 812 may be configured to manage user information (including data describing the user and/or associated credentials such as usernames, passwords, pins, cryptographic keys, and the like) and access policies. Service 812 may authenticate the user (e.g., authenticate credentials received from the user device 810 in the request, prompt the user for credentials via public API 806, etc.) and perform any suitable operations to determine whether the user is authorized to perform operations related to the request. If the user is not authenticated and/or authorized, the service 812 may send data back to controller 814 indicating the user is not authenticated and/or authorized to perform the requested operation. Controller 814 may transmit, via public API 806, an indication to the user device 810 indicating the request was denied (and potentially an indication as to the reason the request was denied). However, if the user is authenticated and authorized, the service 812 may send data, via public API 806, back to the controller 814 indicating that the user is authenticated and authorized to perform the requested operation. Controller 814, upon receiving an indication that the user is authenticated and authorized, may perform any suitable operations to fulfill the request. By way of example, if the request was to create a block volume of a particular size (e.g., 10 GB), the controller 814 may perform any suitable orchestration operations to create a block volume within block storage 820. An indication as to whether the operations were successful or unsuccessful may be transmitted back to the user device 810 via public API 806.

In some embodiments, data store 818 is shared between block storage 820 and object storage 822. In these embodiments, increasing the size of block storage 820 may reduce the amount of storage available for object storage 822, and vice versa.

In some embodiments, controller 814 may be configured to a software defined storage platform (e.g., Ceph) for any suitable create, read, update, and delete (CRUD) operations requested by user device 810, service 808, service 812, or any suitable component of the edge device on which storage control plane 802 operates.

Controller 814 may be configured to provide health status, disk usage, performance metrics, and the like related to the block storage 820. In some embodiments, when the edge device is connected to a cloud environment (e.g., a data center), the controller 814 may perform operations for syncing the data stored in block storage 820 and/or object storage 822 (and/or any suitable files in embodiments in which a file system is utilized within data store 818) to a corresponding component in the cloud environment.

Figure 9:
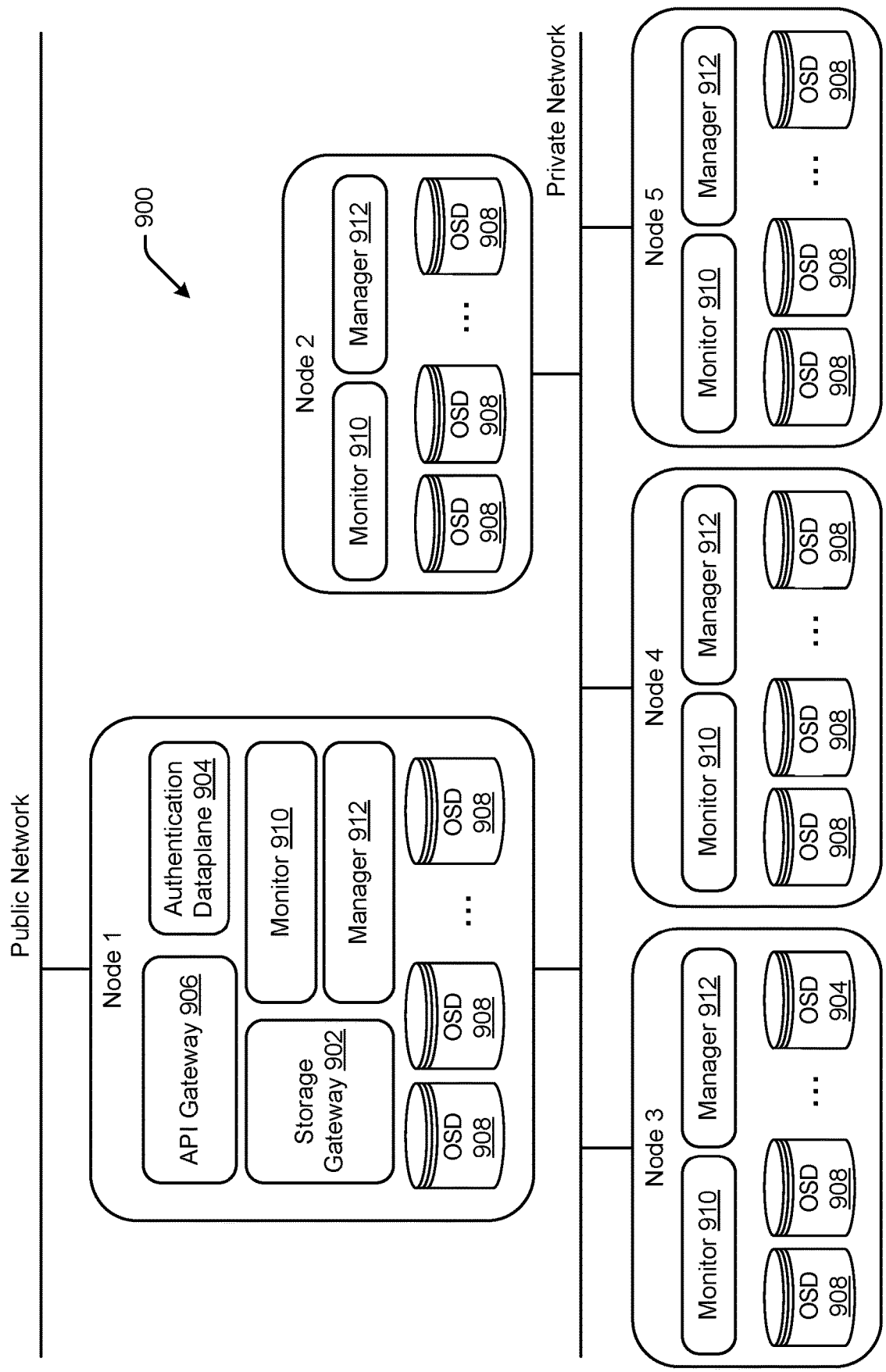
FIG. 9 is a block diagram depicting an example computing cluster including five computing nodes, according to at least one embodiment.

FIG. 9 is a block diagram depicting an example computing cluster 900 including five computing nodes, according to at least one embodiment. Although five computing nodes are depicted, any suitable number of computing nodes (each an example of the edge device 500 of FIG. 5) may be utilized.

Computing cluster 900 may implement a distributed, fault tolerant system (e.g., Ceph) that provides redundancy for object storage, block storage, and VM images. Storage gateway may be an example of public API 806 of FIG. 8. Authentication data plane 904 may be an example of an authentication and/or authorization component that is configured to authenticate (via credentials or otherwise) and/or authorize (via evaluating user information against access policies) a user to perform one or more operations via a storage system (e.g., storage system 800 of FIG. 8) implemented by the computing cluster 900. In some embodiments, storage gateway 902 may be configured to invoke the functionality of authentication data plane 904 to authorize and/or authenticate a requestor (e.g., a user, another service, etc.). In some embodiments, storage gateway 902 may be configured to map data received from a format associated with the public API 806 of FIG. 8 (e.g., an S3-compatible API, an object storage API), to an application programming interface associated with the data store 818 of FIG. 8 (e.g., API gateway 906, an S3-compatible API). Although not depicted, the API gateway 906 and the storage gateway 902 may be implemented on any suitable combination of the computing nodes (e.g., edge devices) of the computing cluster 900.

Although not depicted, each of the computing nodes (nodes 1-5) may implement any suitable number of block devices. By way of example, each node may implement any suitable number of Ceph block devised. A Ceph block device may be a thin-provisioned and resizable data store that is striped over multiple object storage devices (e.g., a subset of the OSDs 908). In some embodiments, node 1 (or any node of the computing cluster 900) may expose an S3-compatible API and/or an object storage API to clients (e.g., via storage gateway 902). Although each of the nodes may implement the gateways 902 and 906, in some embodiments, only one node (as depicted, node 1) may be connected to a public network (e.g., to a data center when connectivity allows).

Some example workloads that may be performed may include:
  Loading large files (e.g., videos) to the object storage 822 of FIG. 8 and performing post-processing using a custom virtual machine (VM) running in the computing cluster. Video analysis may be performed by the computing cluster 900.
  Loading database backup files to the object storage 822, create a custom VM and attach a block storage volume, run the custom VM and instantiate the database using the backup files and the block volume.

Loading data and managing a customer application in an offline mode. Performing a two-way sync with a cloud environment (e.g., a data center) when connectivity is available.

Loading data via NFS mounts or object storage API's (e.g., APIs associated with object storage 822); access via NFS mounts or object storage API's. When combined with syncing, this can serve as a way to achieve data migration from on-site NAS servers to a cloud environment (e.g., an Oracle Cloud Infrastructure (OCI) platform).

Developing applications on-site that use a cloud API (e.g., an OCI API) and migrating to the cloud environment. Similarly, taking customer applications that run against the cloud environment (e.g., OCI) and running them against the object storage 822.

Each computing node of computing cluster 900 may include any suitable number of storage objects (e.g., object storage daemons (OSDs) 908). Clients (e.g., a component or entity that provides an object or data block for storage) connect to an OSD to store data (e.g., block data, an object, etc.). Each OSD works with rules and maps to propagate said data into the computing cluster 900. In some embodiments, OSDs 908 may provide two modes of operation: managing object over a file store (e.g., a file system on top of the OSDs 908) or managing object over dedicated disk per OSD (referred to herein as BlueStore, that puts objects directly on the OSDs 908 without requiring an initial file system). In some embodiments, the OSDs 908 may be configured to manage objects over dedicated disk per OSD by default.

Each computing node of computing cluster 900 may include a respective instance of monitor 910. In some embodiments, only a subset of the computing nodes may include an instance of monitor 910. In some embodiments, an odd number of monitors may be utilized in computing cluster 900 to ensure consensus. Monitor 910 may be configured to monitor OSDs for failures using one or more protocols for solving consensus in a network of unreliable or fallible processors (e.g., PAXOS algorithms). Consensus refers to the process of agreeing, by the computing nodes, on one result among the group. In some embodiments, monitor 910 stores metadata on disk and provides rules and maps to clients and OSDs to enable object (e.g., data block, data object, etc.) reading and writing. In some embodiments, the nodes may be configured to replace monitor(s) that fail (e.g., due to node failure or otherwise) with an equal number of monitors running on other nodes.

In some embodiments, the rules provided/utilized by monitor 910 may be used to control data placement. In some embodiments, these rules may include rules for Controlled Replication Under Scalable Hashing (CRUSH). The rules may allow data placement to be done with the greatest fault tolerance allowed by the configuration. The rules may build a hierarchy (e.g., one or more CRUSH maps) that describes the relationship of the nodes (and/or OSDs) in the computing cluster 900. For example, a CRUSH map may be utilized to specify which OSDs are on a common host, etc. A widely distributed cluster then can be reflected in the rules to allow for the greatest distribution of data as needed for durability and performance. For instance, some data may be required to be replicated across a larger number of OSDs for greatest durability, other data may have replication within a smaller number of OSDs for less durability but shorter time to access.

The computing cluster 900 inherently tolerates OSD failures. If a single OSD in a placement group fails for a short enough period of time (which may be configurable) then the system can access the corresponding data through other OSDs. In the event of a disk failure, the computing cluster will eventually mark the corresponding OSD as being "down" and adjust all placement groups on this OSD so that data automatically backfills to other OSDs. While this backfilling is occurring, data is still accessible but the monitor 910 may indicate that the affected placement groups are running in a "degraded" mode. In some embodiments, backfilling may be disabled on a global basis across the cluster. This can be useful when replacing a node, to prevent objects within placement groups on this node from being copied while the node is being replaced. Once completed, the user can re-enable backfilling.

In some embodiments, when a disk fails, the OSD may be removed (e.g., by the monitor 910) from the cluster map, the failed disk removed from the node, and replaced with a new disk. The new disk may be prepared in a manner as to have the same cluster-wide OSD identity as the previous disk. In some embodiments, detecting a replaced node may cause monitor 910 to begin a background redistribution of data to balance data across the computing cluster 900 which may include populating OSDs on the replacement node.

Each computing node of computing cluster 900 may include a respective instance of manager 912. Manager 912 may be configured to provide health, usage, and performance information related to the health, usage, and performance of the OSDs.

The OSDs 908 on a given node may be referred to herein as a "local pool," while a pool of OSDs composed of multiple of the OSDs 908 on different nodes may be referred to as a "durable pool." A durable pool distributes storage so that disk and/or node failures are tolerated. In some embodiments, data may be replicated to a particular number of nodes (e.g., 3, 5, 2, etc.) or erasure coding may be utilized. Erasure coding refers to a method of data protection in which the data is broken into fragments, expanded, and encoded with redundant data pieces and stored across a set of different OSDs. In some embodiments, the local pool of OSDs may be utilized when running a single edge device, while one or more durable pools may be utilized when a computing cluster of multiple edge devices is utilized. In some embodiments, the CRUSH map provided by the monitor 910 may be utilized to determine how data durability is provided. For example, a CRUSH map for the computing cluster 900 may show a five-node edge device cluster with five hosts and some number of OSDs per host (e.g., 8, 6, 12, etc.). The map and rules provided by monitor 910 may be utilized to distribute objects. This process will be described in more detail with respect to FIG. 11.

Although computing cluster 900 is depicted as utilizing multiple edge devices, a computing cluster may be made up of a single edge device. In a single edge device scenario, the computing cluster would include the set of OSDs on that edge device. The storage platform (e.g., Ceph) configuration may be defined with rules to indicate the lowest level in the hierarchy is disk and not physical node. In this scenario, pools may be created with a maximum size of 1.

In some embodiments, the rules provided by monitor 910 determine how data is distributed, and these rules are bounded by counts of OSDs and placement groups. A stable OSD cluster achieves scalability by distributing this information among all clients and OSDs so objects can be accessed without needing a central resource. In some embodiments, expanding the computing cluster 900 may impact this data distribution and the map may be altered with an addition of new node(s). Once modified, the cluster may need to go thru a redistribution of data. The amount of time this requires is dependent upon the current use of object storage and the amount of change.

Figure 10:
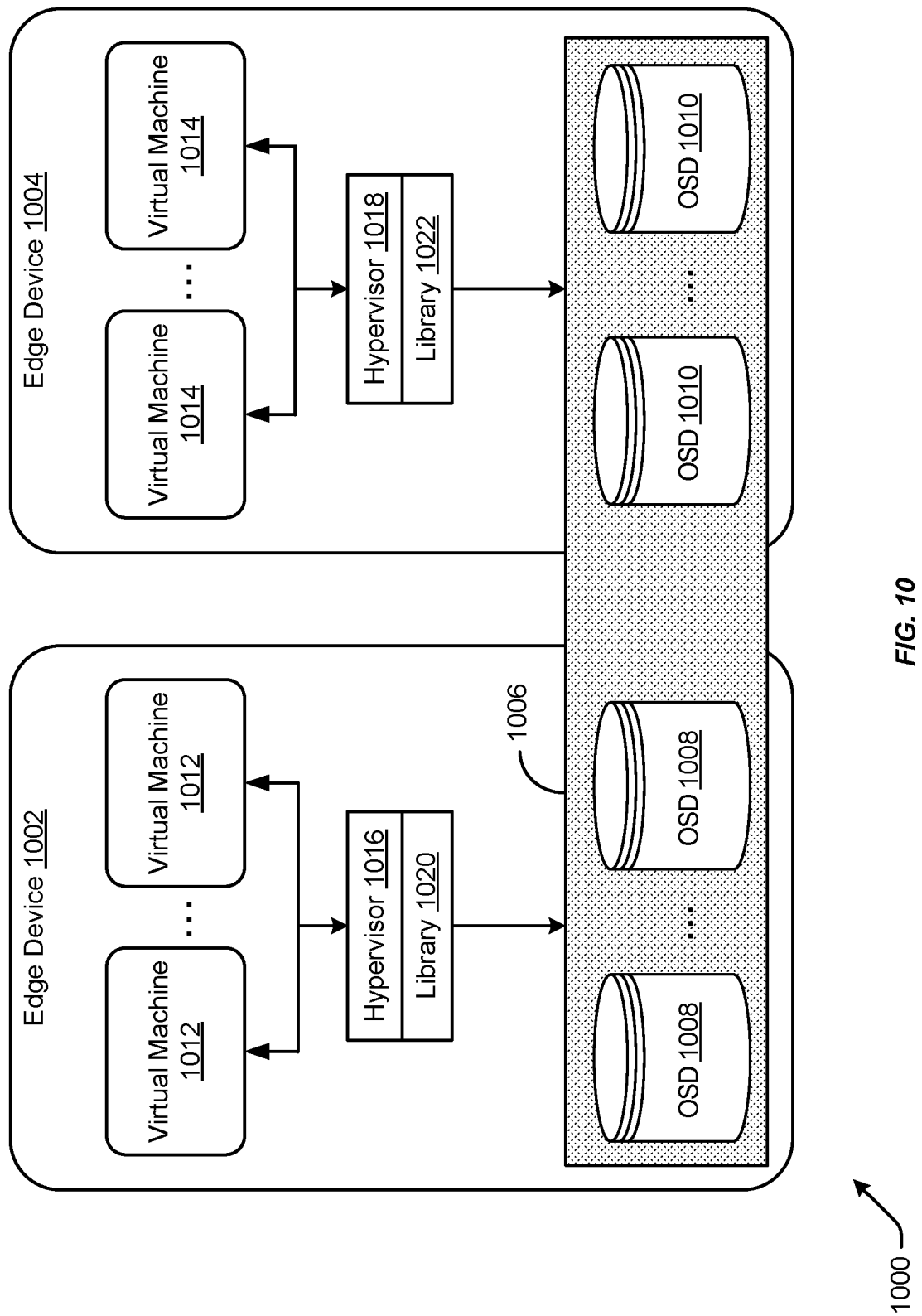
FIG. 10 is a block diagram depicting interactions between virtual machines of respective edge devices and a distributed storage system, according to at least one embodiment.

FIG. 10 is a block diagram depicting interactions between virtual machines of respective edge devices and a distributed storage system, according to at least one embodiment. Edge devices 1002 and 1004 are utilized in FIG. 10 for illustration, although any suitable number of edge devices may be utilized (e.g., 2, 4, 8, etc.). Edge devices 1002 and 1004 are each an example of the edge device 500 of FIG. 5 and may collectively implement a distributed data store (e.g., data store 1006). Data store 1006 may include any suitable number of OSDs 1008 and 1010 (each an example of the OSDs 908 of FIG. 9). OSDs 1008 may be a set of OSDs implemented by edge device 1002. OSDs 1010 may be a set of OSDs implemented by edge device 1004. Each of the edge devices may execute any suitable number of virtual machines. For example, edge device 1002 may execute virtual machines 1012 (e.g., a set of one or more virtual machines) and edge device 1004 may execute virtual machines 1012 (e.g., a set of one or more virtual machines). The virtual machines 1012 and 1014 may be each be an example of the VMs 508 of FIG. 5.

The virtual machines 1012 and 1014 may each be managed by hypervisors 1016 and 1018, respectively. In some embodiments, hypervisors 1016 and 1018 may be provided by one or more services of the edge device (e.g., service(s) 502 of FIG. 5). In some embodiments, hypervisors 1016 and 1018 may be machine emulators (e.g., Quick EMUlator (QEMU)) that can run operating systems and programs for one machine on a different machine. Hypervisors 1016 and 1018 may also be configured to interoperate with kernel-based virtual machines (KVM) and provide emulation for user-level processes, allowing application compiled for one architecture to run on another. In some embodiments, hypervisors 1016 and 1018 can pass a block device (e.g., ODS 1008 and 1010, respectively) from the host on to a guest. Hypervisors 1016 and 1018 can access OSDs 1008 and 1010, respectively, via library 1024 and library 1026, respectively. Libraries 1024 and 1026 may be configured to define access functions to OSDs 1008 and 1010, respectively. By way of example, each of the OSDs of FIG. 10 (as well as those of FIG. 9) may individually be Reliable Autonomic Distributed Object Store (RADOS) block devices that make use of the libRBD library. In some embodiments, hypervisors 1016 and 1018 can be used to convert existing virtual machine images previously stored locally to block storage device images (e.g., Ceph block device images).

Figure 11:
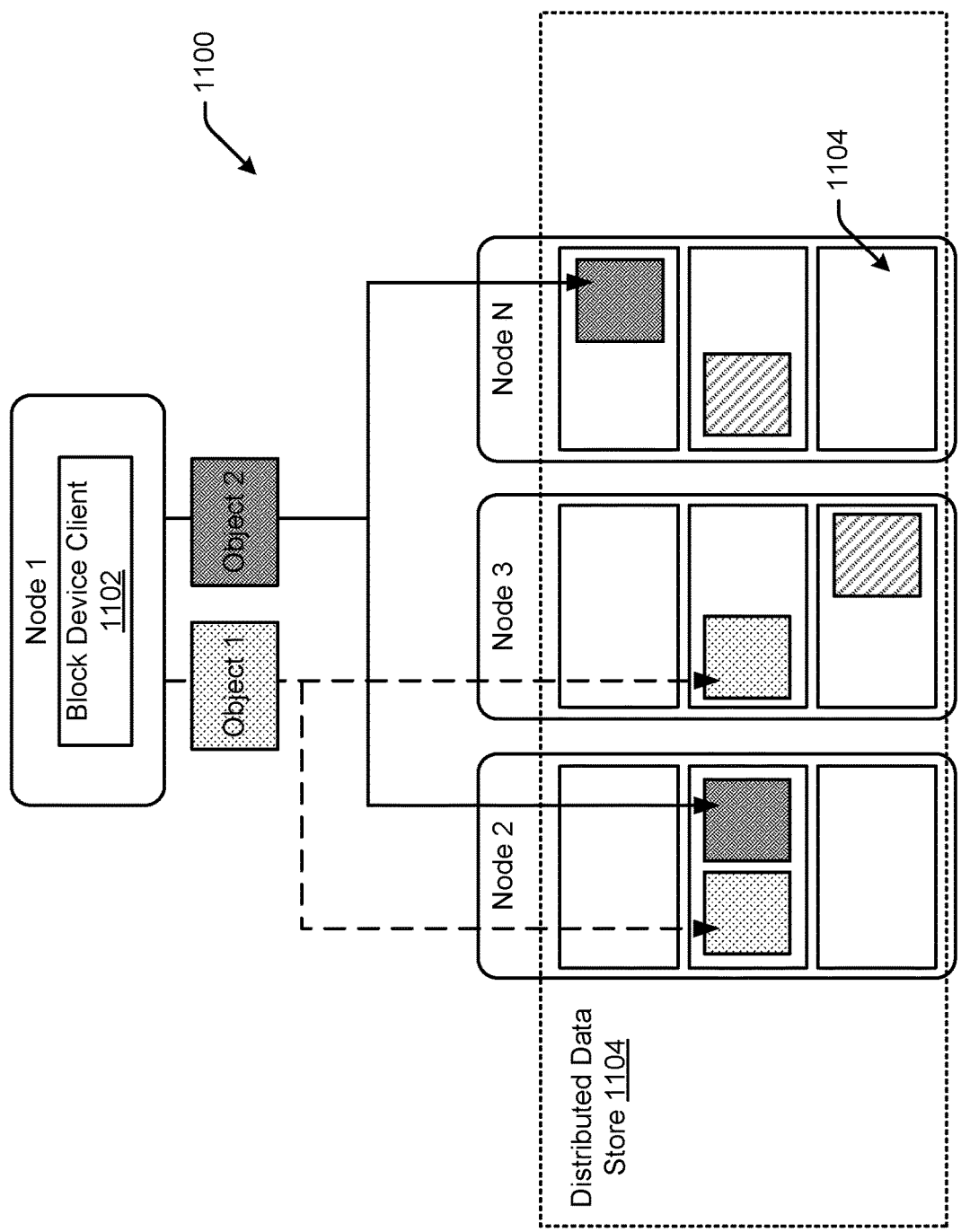
FIG. 11 is a block diagram that illustrates techniques for distributing data in a computing cluster, according to at least one embodiment.

FIG. 11 is a block diagram that illustrates techniques for distributing data in a computing cluster 1100, according to at least one embodiment. Computing cluster 1100 may be an example of the computing cluster 900 of FIG. 9. Nodes 1-N may include any suitable number of computing nodes, each being an example of the computing nodes of FIG. 9. Block device client 1102 may be an example of controller 814 of FIG. 8. In some embodiments, block device client 1102 may stripe data to be stored in distributed data store 1104. Distributed data store 1104 may include any suitable number of OSDs (of which OSD 1106 is an example). Each of the OSDs depicted in FIG. 11 may individually be an example of the OSDs 908 of FIG. 9.

In some embodiments, the block device client 1102 distribute data based on pools, each of which may be associated with an object placement rule (e.g., a CRUSH object placement rule). In some embodiments, the object placement rules create pools that span all OSDs in the cluster, i.e. all disks, and use replication (e.g., store two or more copies of the same data on different OSDs). Custom object placement rules can be created to use erasure coding or restrict a pool to only certain OSDs. In some embodiments, the distributed data store 1104 stores, replicates, and rebalances data objects across the cluster dynamically.

In some embodiments, the block device client 1102 may stripe images into data objects (e.g., RADOS objects) to be stored in the distributed data store 1104. In some embodiments, the data (e.g., images) may be striped into objects (e.g., RADOS objects such as object 1 and object 2 of FIG. 11) of a predefined size (e.g., 4 MB by default). The block device client 1102 may be configured to map objects 1 and 2 into placement groups which are then stored on various OSDs. By way of example, the example depicted in FIG. 11 depicts a replication factor of 2 (indicating each object is to be stored on two different OSDs, on at least two different nodes) although any suitable replication factor (e.g., 3, 5, 7, etc.) may be utilized.

In some embodiments, distributing data to the distributed data store 1104 may utilize pools, which are logical groups for storing objects. Pools may be utilized to manage the number of placement groups, the number of replicas, and/or the placement rule (e.g., CRUSH rule) for the pool. In some embodiments, the block device client (e.g., which may include monitor 910 of FIG. 9) may map objects (e.g., objects 1 and 2) to placement groups. Placement groups (PGs) may be shards or fragments of a logical object pool that place objects as a group into OSDs. Placement groups reduce the amount of per-object metadata when objects are stored the data in OSDs. A larger number of placement groups (e.g., 100 per OSD) leads to better balancing.

Block device client 1102 (including monitor 910) may include a map (not depicted) (e.g., a CRUSH map). In some embodiments, this map may describe the physical topology of the distributed data store to a distribution algorithm (e.g., the CRUSH algorithm) to determine at which node(s) the data for an object and its replicas should be stored, and how to do so across failure domains for added data safety among other things.

Distributed data store 1104 may implement a balancer that may be configured to automatically optimize the distribution of placement groups across devices (e.g., OSDs) to achieve a balanced data distribution. A balanced data distribution may maximize the amount of data that can be stored in the distributed data store 1104 and evenly distributing the workload across OSDs.

In some embodiments, placement groups are similar to "buckets" to for distributing objects. In some embodiments, a hash-bucketing operation may be utilized with the object (e.g., the name of object 1). For example, an object name of object 1 may be unique and can be used as a hash key over the rule to select one or more particular OSDs that are to store a copy of object 1. A placement group is then the modulo of the hash.

Figure 12:
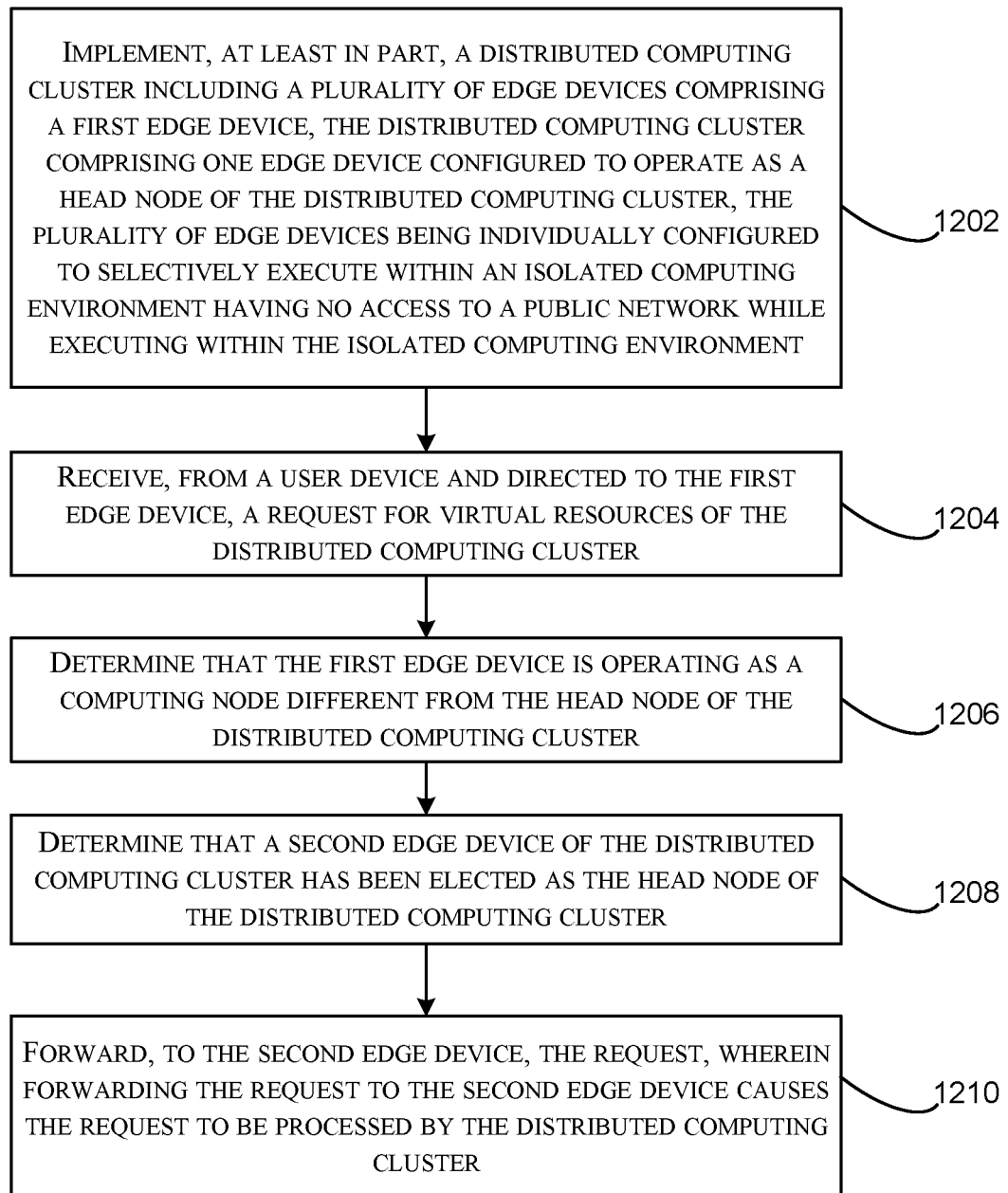
FIG. 12 is a block diagram illustrating an example method for processing a request for virtual resource by a distributed computing cluster, in accordance with at least one embodiment.

FIG. 12 is a block diagram illustrating an example method 1200 for processing a request for virtual resource by a distributed computing cluster, in accordance with at least one embodiment. The operations of method 1200 may be performed in any suitable order. Although a particular number of operations are illustrated, the method 1200 may include more or fewer operations than those depicted. In some embodiments, the method 1200 may be performed by an edge device (e.g., edge device 500 of FIG. 5). The edge device may be operating as a computing node of a distributed computing cluster (e.g., computing cluster 900 of FIG. 9).

The method 1200 may begin at 1202, where a distributed computing cluster including a plurality of edge devices comprising a first edge device (e.g., the edge device 500 of FIG. 5) may be implemented (at least in part by the first edge device). In some embodiments, the distributed computing cluster may comprise one edge device configured to operate as a head node of the distributed computing cluster (e.g., the computing cluster 900). In some embodiments, the plurality of edge devices may be individually configured to selectively execute within an isolated computing environment such that the edge devices may have no access to a public network while executing within the isolated computing environment.

At 1204, a request for virtual resources of the distributed computing cluster may be received (e.g., by the storage control plane 802 of FIG. 8). The request may be received from a user device (e.g., user device 810 of FIG. 8) and directed to the first edge device.

At 1206, the first edge device may determine that the first edge device is operating as a computing node different from the head node of the distributed computing cluster. By way of example, the first edge device may be node 2 of FIG. 2, which initially may be a different computing node than the one currently acting as the head node (e.g., node 1 of FIG. 9, for example).

At 1208, the first edge device may determine that a second edge device (e.g., node 1 of FIG. 900) of the distributed computing cluster has been elected as the head node of the distributed computing cluster. In some embodiments, monitor 910 of the first edge device may be configured to contact a state data store (e.g., state storage 816) which may be configured to store and provide by request a current head node of the computing cluster.

At 1210, with the current head node identified, the first edge node may forward the request to the second edge device. In some embodiments, forwarding the request to the second edge device causes the request to be processed by the distributed computing cluster.

In some embodiments, the first edge device and the second edge device, and any other edge device of the plurality of edge devices may provide a plurality of object storage devices for data replication (e.g., according to the data distribution and replication rules discussed above in connection with FIG. 11). In some embodiments, the distributed computing cluster stores key-value pairs where the key-value pairs are individually replicated on at least two of the plurality of object storage devices. In some embodiments, the first edge device exposes a public application programming interface accessible to the user device. The user device may access remaining edge devices of the plurality of edge devices through the public application programming interface.

It should be appreciated that, in some embodiments, any suitable computing node of the cluster may process the request if the request is a read request. However, if the request is a write request, the request may be forwarded to the identified head node as described above. In some embodiments, if the request is a read request, the first edge device may transmit the read request to any suitable number of the computing nodes in the cluster. The first edge device may then receive, from a subset of the distributed computing cluster, a number of response to the read request. In some embodiments, the first edge device may identify that a majority (or some threshold number) of the edge devices of the distributed computing cluster have responded. In response to identifying that the majority of the distributed computing cluster have responded, the first edge device may transmit an indication that the read request was successful.

It should be appreciated that the head node of the cluster is not static and may change. At any suitable time, the computing nodes of the cluster may perform any suitable leader election algorithm to identify a head node for the cluster. Thus, in some embodiments, the method 1200 may further include receiving, from a second user device and directed to the first edge device, a second request for virtual resources of the distributed computing cluster. The first edge device could then determine that a third edge device (e.g., node 2, a node different from the previous head node, node 1) of the distributed computing cluster has been elected as the head node of the distributed computing cluster. In response to this determination, the first edge device may forward the second request to the third edge device (e.g., the current head node). In some embodiments, forwarding the second request to the third edge device causes the second request to be processed by the distributed computing cluster.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or modules are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A method, comprising:
    implementing, at least in part by a first edge device, a distributed computing cluster including a plurality of edge devices comprising the first edge device, the distributed computing cluster comprising a particular edge device configured to operate as a head node of the distributed computing cluster, the plurality of edge devices being individually configured to selectively execute within an isolated computing environment, the plurality of edge devices having no access to a public network while executing within the isolated computing environment;
    receiving, by the first edge device, a request for utilizing the distributed computing cluster;
    determining, by the first edge device, whether the first edge device is configured to operate as the head node of the distributed computing cluster; and
    processing or forwarding, by the first edge device, the request based at least in part on determining whether the first edge device is configured to operate as the head node of the distributed computing cluster.

2. The method of claim 1, wherein each of the plurality of edge devices provide one or more respective storage devices of a plurality of storage devices.

3. The method of claim 2, wherein the distributed computing cluster stores key-value pairs, and wherein the key-value pairs are individually replicated on at least two of the plurality of storage devices.

4. The method of claim 1, wherein the head node is determined to be a second edge device that is different from the first edge device, and wherein the method further comprises:
    determining, by the first edge device, whether the request is a read request or a write request, wherein the request is forwarded to the second edge device based at least in part on determining the request is the write request; or
    processing, by the first edge device, the request based at least in part on determining the request is the read request.

5. The method of claim 4, wherein the request is the read request, and wherein processing the request further comprises:
    transmitting, by the first edge device, the read request to a set of computing nodes of the distributed computing cluster, the set of computing nodes each corresponding to a corresponding edge device of the distributed computing cluster;
    receiving, by the first edge device from a subset of set of computing nodes of the distributed computing cluster, a number of responses to the read request;
    identifying, by the first edge device, that a majority of the set of computing nodes have responded; and
    in response to identifying that the majority of the set of computing nodes have responded, transmitting, by the first edge device, an indication that the read request was successful.

6. The method of claim 1, wherein the first edge device is determined to be the head node, and wherein the first edge device exposes a public application programming interface, and wherein the public application programming interface allows access to remaining edge devices of the plurality of edge devices.

7. The method of claim 1, wherein different edge devices transition to operate as the head node of the distributed computing cluster over time.

8. An edge device, comprising:
    one or more processors; and
    one or more memories configured with computer-executable instructions that, when executed by the one or more processors, cause the edge device to:
    implement, at least in part, a distributed computing cluster including a plurality of edge devices comprising the edge device, the distributed computing cluster comprising a particular edge device configured to operate as a head node of the distributed computing cluster, the plurality of edge devices being individually configured to selectively execute within an isolated computing environment, the plurality of edge devices having no access to a public network while executing within the isolated computing environment;

receive a request for utilizing the distributed computing cluster;

determine whether the edge device is configured to operate as the head node of the distributed computing cluster; and process or forward the request based at least in part on determining whether the edge device is configured to operate as the head node of the distributed computing cluster.

9. The edge device of claim 8, wherein each of the plurality of edge devices provide one or more respective storage devices of a plurality of storage devices.

10. The edge device of claim 9, wherein the distributed computing cluster stores key-value pairs, and wherein the key-value pairs are individually replicated on at least two of the plurality of storage devices.

11. The edge device of claim 8, wherein the head node is determined to be a second edge device that is different from the edge device, and wherein executing the computer-executable instructions further causes the edge device to:

determine whether the request is a read request or a write request, wherein the request is forwarded to the second edge device based at least in part on determining the request is the write request; or process the request based at least in part on determining the request is the read request.

12. The edge device of claim 11, wherein the request is the read request, and wherein computer-executable instructions for processing the request further causes the edge device to:

transmit the read request to a set of computing nodes of the distributed computing cluster, the set of computing nodes each corresponding to a corresponding edge device of the distributed computing cluster;

receive, from a subset of set of computing nodes of the distributed computing cluster, a number of responses to the read request;

identify that a majority of the set of computing nodes have responded; and in response to identifying that the majority of the set of computing nodes have responded, transmit an indication that the read request was successful.

13. The edge device of claim 8, wherein the edge device is determined to be the head node, and wherein the edge device exposes a public application programming interface, and wherein the public application programming interface allows access to remaining edge devices of the plurality of edge devices.

14. The edge device of claim 8, wherein different edge devices of the plurality of edge devices operate as the head node of the distributed computing cluster over time.

15. A non-transitory computer-readable medium comprising computer-executable instructions that, when executed with one or more processors of an edge device, cause the edge device to:

implement, at least in part, a distributed computing cluster including a plurality of edge devices comprising the edge device, the distributed computing cluster comprising a particular edge device configured to operate as a head node of the distributed computing cluster, the plurality of edge devices being individually configured to selectively execute within an isolated computing environment, the plurality of edge devices having no access to a public network while executing within the isolated computing environment;

receive a request for utilizing the distributed computing cluster;

determine whether the edge device is configured to operate as the head node of the distributed computing cluster; and process or forward the request based at least in part on determining whether the edge device is configured to operate as the head node of the distributed computing cluster.

16. The non-transitory computer-readable medium of claim 15, wherein each of the plurality of edge devices provide one or more respective storage devices of a plurality of storage devices.

17. The non-transitory computer-readable medium of claim 16, wherein the distributed computing cluster stores key-value pairs, and wherein the key-value pairs are individually replicated on at least two of the plurality of storage devices.

18. The non-transitory computer-readable medium of claim 15, wherein the head node is determined to be a second edge device that is different from the edge device, and wherein executing the computer-executable instructions further causes the edge device to:

determine whether the request is a read request or a write request, wherein the request is forwarded to the second edge device based at least in part on determining the request is the write request; or process the request based at least in part on determining the request is the read request.

19. The non-transitory computer-readable medium of claim 15, wherein the edge device is determined to be the head node, and wherein the edge device exposes a public application programming interface, and wherein the public application programming interface allows access to remaining edge devices of the plurality of edge devices.

20. The non-transitory computer-readable medium of claim 15, wherein different edge devices of the plurality of edge devices operate as the head node of the distributed computing cluster over time.

* * * * *